(12) United States Patent
Harada

(10) Patent No.: US 12,239,415 B2
(45) Date of Patent: Mar. 4, 2025

(54) IMAGING SUPPORT DEVICE, OPERATION METHOD FOR THE SAME, AND OPERATION PROGRAM

(71) Applicant: FUJIFILM CORPORATION, Tokyo (JP)

(72) Inventor: Daiki Harada, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 250 days.

(21) Appl. No.: 17/950,107

(22) Filed: Sep. 22, 2022

(65) Prior Publication Data

US 2023/0015698 A1 Jan. 19, 2023

Related U.S. Application Data

(63) Continuation of application No. PCT/JP2021/009922, filed on Mar. 11, 2021.

(30) Foreign Application Priority Data

Mar. 30, 2020 (JP) ................................ 2020-061592

(51) Int. Cl.
*A61B 5/00* (2006.01)
*A61B 6/00* (2024.01)
(Continued)

(52) U.S. Cl.
CPC .......... *A61B 5/0077* (2013.01); *A61B 5/0035* (2013.01); *A61B 5/7425* (2013.01);
(Continued)

(58) Field of Classification Search
CPC ... A61B 5/0077; A61B 5/0035; A61B 5/7423; A61B 5/743; A61B 6/08; A61B 6/4417;
(Continued)

(56) References Cited

U.S. PATENT DOCUMENTS

| 5,539,798 A | 7/1996 | Asahina et al. |
| 2013/0121468 A1 | 5/2013 | Ohta et al. |

(Continued)

FOREIGN PATENT DOCUMENTS

| JP | H06-217973 A | 8/1994 |
| JP | 2004-121369 A | 4/2004 |

(Continued)

OTHER PUBLICATIONS

International Search Report issued in International Application No. PCT/JP2021/009922 on Jun. 1, 2021.
(Continued)

*Primary Examiner* — Mark R Gaworecki
(74) *Attorney, Agent, or Firm* — SOLARIS Intellectual Property Group, PLLC

(57) ABSTRACT

An imaging support device used in a radiography apparatus including a radiation source and a radiation image detector that detects a radiation image of a subject on the basis of radiation emitted from the radiation source and transmitted through the subject includes an optical camera that outputs an optical image by optically imaging a region including an irradiation field of the radiation applied to the subject from the radiation source, and at least one processor, in which the processor associates the optical image acquired by the optical camera with the radiation image on the basis of a timing signal transmitted from the radiation image detector side.

7 Claims, 16 Drawing Sheets

(51) Int. Cl.
  *A61B 6/08* (2006.01)
  *A61B 6/58* (2024.01)
  *A61B 6/04* (2006.01)
  *A61B 6/42* (2024.01)

(52) U.S. Cl.
  CPC ............... *A61B 5/743* (2013.01); *A61B 6/08* (2013.01); *A61B 6/4417* (2013.01); *A61B 6/54* (2013.01); *A61B 6/542* (2013.01); *A61B 6/587* (2013.01); *A61B 6/04* (2013.01); *A61B 6/4233* (2013.01); *A61B 6/4405* (2013.01); *A61B 6/4464* (2013.01); *A61B 6/588* (2013.01); *A61B 6/589* (2013.01); *A61B 2505/09* (2013.01)

(58) Field of Classification Search
  CPC ........... A61B 6/54; A61B 6/542; A61B 6/587; A61B 6/04; A61B 6/4233; A61B 6/4405; A61B 6/4464; A61B 6/588; A61B 6/589; A61B 2505/09
  See application file for complete search history.

(56) References Cited

U.S. PATENT DOCUMENTS

| | | |
|---|---|---|
| 2013/0208851 A1 | 8/2013 | Kimoto et al. |
| 2018/0125605 A1* | 5/2018 | Kim-Whitty ........ A61B 6/5229 |
| 2019/0046130 A1 | 2/2019 | Imamura et al. |
| 2019/0046134 A1* | 2/2019 | Imamura ................ A61B 6/465 |
| 2019/0069871 A1* | 3/2019 | Tkaczyk .............. A61B 6/4452 |
| 2019/0231433 A1* | 8/2019 | Amanatullah ..... A61B 17/1703 |

FOREIGN PATENT DOCUMENTS

| | | |
|---|---|---|
| JP | 2008-206740 A | 9/2008 |
| JP | 2011-024721 A | 2/2011 |
| JP | 2011-139761 A | 7/2011 |
| JP | 2012-029916 A | 2/2012 |
| JP | 2014-117368 A | 6/2014 |
| JP | 2019-033830 A | 3/2019 |
| JP | 2019-097769 A | 6/2019 |

OTHER PUBLICATIONS

Written Opinion of the ISA issued in International Application No. PCT/JP2021/009922 on Jun. 1, 2021.
English language translation of the following: Office action dated Aug. 1, 2023 from the JPO in a Japanese patent application No. 2022-511762 corresponding to the instant patent application.
Extended European Search Report dated Aug. 24, 2023, issued in corresponding EP Patent Application No. 21779977.4.

* cited by examiner

IMAGING SUPPORT DEVICE, OPERATION METHOD FOR THE SAME, AND OPERATION PROGRAM

CROSS-REFERENCE TO RELATED APPLICATIONS

This application is a continuation application of International Application No. PCT/JP2021/009922, filed on Mar. 11, 2021, the disclosure of which is incorporated herein by reference in its entirety. Further, this application claims priority from Japanese Patent Application No. 2020-061592, filed on Mar. 30, 2020, the disclosure of which is incorporated herein by reference in its entirety.

BACKGROUND

1. Technical Field

The technique of the present disclosure relates to an imaging support device, an operation method for the same, and an operation program.

2. Description of the Related Art

In a radiography system used in the medical field, a radiologist or a doctor (hereinafter referred to as a technician or the like) positions an imaging site of a subject in preparation for imaging, and then radiography is performed on the basis of instructions from the technician or the like. However, after positioning an imaging site with respect to an irradiation field of radiation and before radiography is performed, the subject may move to cause a misregistration of an imaging site, and an image of a desired imaging site may not be obtained. As described above, a failure to obtain a desired radiation image through radiography, that is, a failure in radiography is referred to as an "imaging failure". In a case where there is imaging failure, reimaging will be performed. A technician or the like may mistakenly determine that an imaging failure occurs in a radiation image that does not need to be reimaged, and thus unnecessary reimaging may be performed. Reimaging takes time and effort, and an amount of exposure of the subject increases, and the number of times of reimaging is preferably small.

In relation to such reimaging, JP2008-206740A discloses a radiography system provided with an optical camera that captures an optical image of an exposed region (hereinafter, also referred to as an optical image) in which radiation is applied to a subject during radiation generation by a radiation generation unit. In the radiography system disclosed in JP2008-206740A, an optical image captured at the same time as a radiation image of a subject captured in the past is stored, and the degree of difference between a position of the subject in the past optical image and a position of the subject in the current optical image is calculated. Consequently, when a new subject is imaged, a position of the subject can be aligned by using the image content of the optical images.

JP1994-217973A (JP-H6-217973A) discloses an X-ray imaging apparatus provided with an optical camera that captures a surface image (hereinafter, also referred to as an optical image) of a subject including an X-ray irradiation field. In the X-ray imaging apparatus disclosed in JP1994-217973A (JP-H6-217973A), a timing control unit controls a timing of storing an X-ray image and a surface image in response to an exposure signal from an X-ray control unit during X-ray imaging, and stores the X-ray image and the surface image related to the same target site in a frame memory in association with each other.

SUMMARY

Depending on an imaging site of a subject, even though a technician or the like thinks that positioning is accurate, actual positioning is not performed properly, and as a result, there is a slight misregistration that causes an imaging failure. For example, in a case of diagnosing a state of a knee joint on the basis of a radiation image of the knee as an imaging site, a joint cavity (gap between bones) needs to be clearly depicted in the radiation image. However, since radiation is a flux of light that radially diverges from a focal point of a radiation source, an incident angle of the radiation may change due to a slight misregistration of the joint, and thus the depiction of the joint cavity may become unclear. In a case where the depiction of the joint cavity is unclear, an imaging failure will occur and reimaging will be required.

In general, even in a case where a radiation image for which reimaging is required to be determined to be necessary is obtained, there are cases where improvement is not expected even in a case where reimaging is performed depending on a subject, and thus it is required to be determined that reimaging is unnecessary. For that determination, it is desirable to be able to refer to a radiation image and an optical image generated at the same time during the previous examination of a subject.

According to the techniques disclosed in JP2008-206740A and JP1994-217973A (JP-H6-217973A), when reimaging is performed, a technician or the like can reposition a subject by referring to an optical image captured at the same time as a radiation image in the past. In order to accurately position the subject, the optical image is required to be captured at the same time as the radiation image in which an imaging failure has occurred. In particular, as described above, in a case where knee joint is used as an imaging site, a slight misregistration of a subject causes an imaging failure, and thus an optical image and a radiation image are desirably captured at the same time as possible.

JP2008-206740A discloses that an optical image captured at the same time as a radiation image of a subject is captured is stored, but does not disclose a specific method of acquiring the radiation image and the optical image at the same time.

JP1994-217973A (JP-H6-217973A) discloses that a timing of storing an X-ray image and a surface image is controlled in response to an exposure signal from the X-ray control unit. The exposure signal is output by pressing an exposure switch. Thus, there is a time lag between the output of the exposure signal from the X-ray control unit and actual emission of X-rays from an X-ray tube. In JP1994-217973A (JP-H6-217973A), an X-ray film is used as a radiation detector. In a case where an electronic cassette is used instead of the X-ray film, there may be a further time lag between the time when the exposure switch is pressed and the time when the electronic cassette is ready for radiation detection.

Therefore, as disclosed in JP1994-217973A (JP-H6-217973A), in a case where an optical image is captured in response to an exposure signal, there is a time lag between the output of the exposure signal and detection of radiation by the radiation detector. Therefore, there is a possibility that there may be a difference between acquisition times of the radiation image and the optical image.

An object of the technique of the present disclosure is to provide an imaging support device, an operation method for the same, and an operation program capable of reducing a difference between acquisition times of a radiation image and an optical image.

In order to achieve the above object, according to the present disclosure, there is provided an imaging support device used in a radiography apparatus including a radiation source and a radiation image detector that detects a radiation image of a subject on the basis of radiation emitted from the radiation source and transmitted through the subject, the imaging support device including an optical camera that outputs an optical image by optically imaging a region including an irradiation field of the radiation applied to the subject from the radiation source; and at least one processor, in which the processor associates the optical image acquired by the optical camera with the radiation image on the basis of a timing signal transmitted from the radiation image detector side.

It is preferable that the timing signal is an irradiation start detection signal output from the radiation image detector having a radiation irradiation start detection function.

It is preferable that the timing signal is a radiation detection signal output from an automatic exposure controller provided separately from the radiation image detector.

It is preferable that the timing signal is a ready signal output that is in a case where the radiation image detector is ready to detect radiation.

It is preferable that the optical camera is a motion picture capturing device that acquires the optical image for each frame and outputs a motion picture formed of the acquired plurality of frames, and the processor extracts one frame from the motion picture on the basis of the timing signal transmitted from the radiation image detector side, and associates the extracted frame with the radiation image.

It is preferable that the processor discards frames other than the extracted frame.

It is preferable that the processor associates patient information with the associated optical image and radiation image and outputs the optical image and the radiation image to the outside.

According to the present disclosure, there is provided operation method for an imaging support device used in a radiography apparatus including a radiation source and a radiation image detector that detects a radiation image of a subject on the basis of radiation emitted from the radiation source and transmitted through the subject, the imaging support device including an optical camera that outputs an optical image by optically imaging a region including an irradiation field of the radiation applied to the subject from the radiation source, the operation method including associating the optical image acquired by the optical camera with the radiation image on the basis of a timing signal transmitted from the radiation image detector side.

According to the present disclosure, there is provided an operation program for operating an imaging support device used in a radiography apparatus including a radiation source and a radiation image detector that detects a radiation image of a subject on the basis of radiation emitted from the radiation source and transmitted through the subject, the imaging support device including an optical camera that optically images a region including an irradiation field of the radiation applied to the subject from the radiation source and at least one processor, the operation program causing the processor to execute associating the optical image acquired by the optical camera with the radiation image on the basis of a timing signal transmitted from the radiation image detector side.

According to the technique of the present disclosure, it is possible to provide an imaging support device, an operation method for the same, and an operation program capable of reducing a difference between acquisition times of a radiation image and an optical image.

BRIEF DESCRIPTION OF THE DRAWINGS

Exemplary embodiments according to the technique of the present disclosure will be described in detail based on the following figures, wherein.

DETAILED DESCRIPTION

First Embodiment

Figure 1:
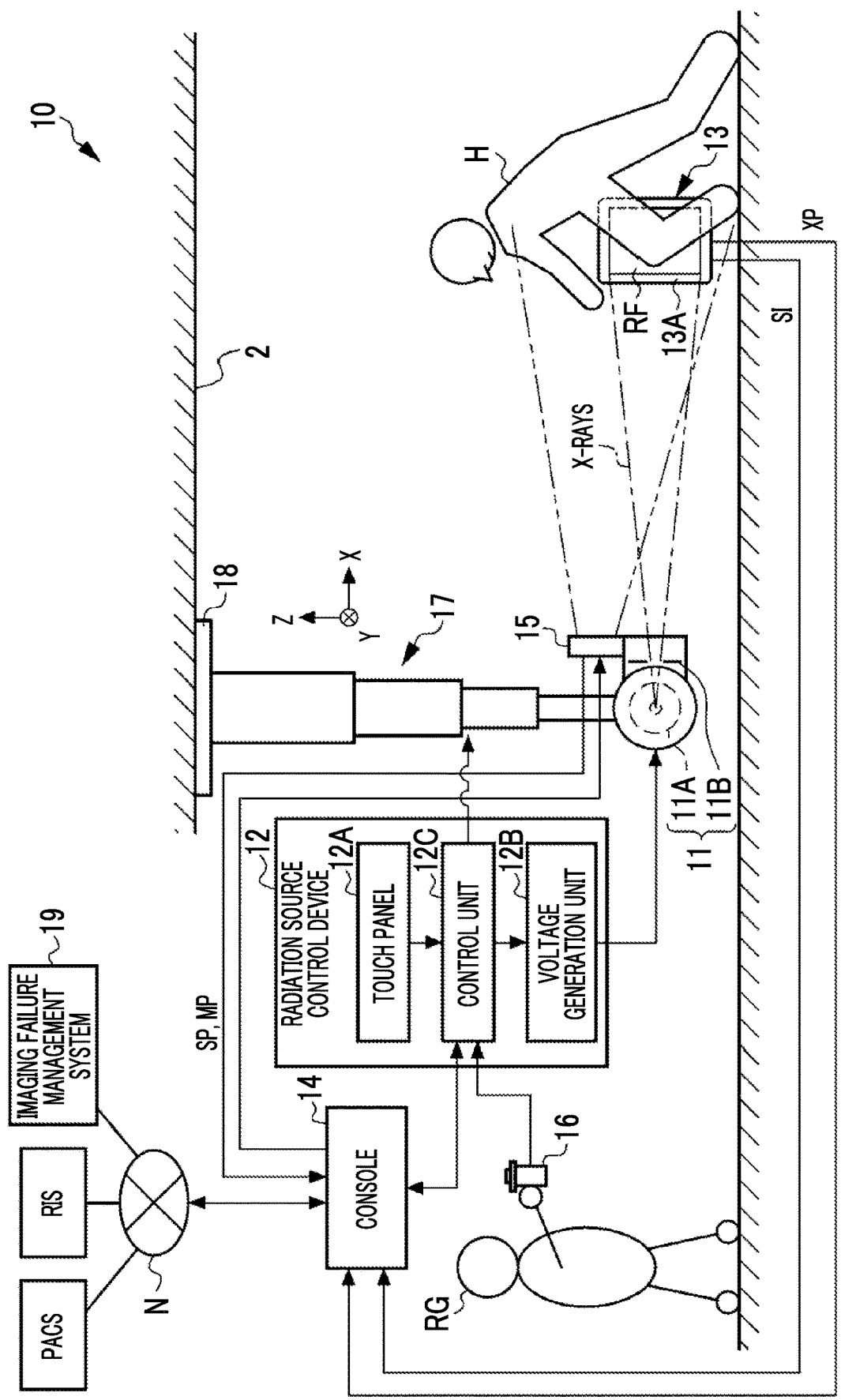
FIG. 1 is a diagram showing a configuration of an X-ray imaging system.

FIG. 1 shows a configuration of an X-ray imaging system 10 that uses X-rays as radiation. The X-ray imaging system 10 using X-rays as radiation includes an X-ray source 11, a radiation source control device 12, an electronic cassette 13, a console 14, and an optical camera 15. In the present embodiment, an imaging support device is configured by the console 14 and the optical camera 15. The X-ray source 11 is an example of a radiation source. The electronic cassette 13 is an example of a radiation image detector.

In the X-ray imaging system 10, the electronic cassette 13 is disposed at a position facing the X-ray source 11. By disposing a subject H between the X-ray source 11 and the electronic cassette 13, it is possible to capture an X-ray image of an imaging site (knee in FIG. 1) of the subject H. The X-ray source 11 and the electronic cassette 13 configure an X-ray imaging apparatus. This X-ray imaging apparatus is an example of a radiography apparatus according to the technique of the present disclosure.

The electronic cassette 13 may be arranged on a standing position imaging table or a lying position imaging table. In the present embodiment, it is assumed that a radiologist (hereinafter, simply referred to as a technician) RG positions the subject H, and then the technician RG performs an X-ray imaging operation.

The X-ray source 11 includes an X-ray tube 11A that generates X-rays and an irradiation field limiter 11B that limits an irradiation field RF that is a region irradiated with X-rays. The X-ray source 11 may include an irradiation field display light source (not shown) that emits irradiation field display light indicating the irradiation field RF on an X-ray incident surface 13A of the electronic cassette 13.

The X-ray tube 11A has a filament that emits thermions and a target that collides with the thermions emitted from the filament and emits X-rays. In the irradiation field limiter 11B, for example, by disposing four lead plates that shield X-rays on respective quadrangular sides, a quadrangular irradiation opening for transmitting X-rays is formed at the center. In this case, the irradiation field limiter 11B changes a size of the irradiation opening by moving positions of the lead plates, and sets the irradiation field RF.

The radiation source control device 12 has a touch panel 12A, a voltage generation unit 12B, and a control unit 12C. The touch panel 12A is operated by the technician RG in a case where X-rays irradiation conditions and a size of the irradiation opening of the irradiation field limiter 11B are set. The X-ray irradiation conditions include a tube voltage and a tube current applied to the X-ray source 11, and the X-ray irradiation time.

The voltage generation unit 12B generates a tube voltage applied to the X-ray tube 11A. By controlling an operation of the voltage generation unit 12B, the control unit 12C sets the tube voltage, the tube current, and the X-ray irradiation time to values set by using the touch panel 12A. The control unit 12C has a timer that starts clocking in a case where X-rays are generated from the X-ray tube 11A. The control unit 12C stops the operation of the X-ray tube 11A, for example, when the time measured by the timer reaches the irradiation time defined in the irradiation conditions. The control unit 12C operates the irradiation field limiter 11B, and sets the size of the irradiation opening to a size set by using the touch panel 12A.

An irradiation switch 16 is connected to the control unit 12C via a cable or the like. The irradiation switch 16 is operated by the technician RG in a case where irradiation of X-rays is started. In a case where the irradiation switch 16 is operated, the radiation source control device 12 generates X-rays in the X-ray tube 11A. Consequently, X-rays are applied toward the irradiation field RF.

The electronic cassette 13 detects an X-ray image XP on the basis of X-rays emitted from the X-ray source 11 and transmitted through the imaging site of the subject H. The electronic cassette 13 has a wireless communication unit and a battery, and performs an operation wirelessly. The electronic cassette 13 wirelessly transmits the detected X-ray image XP to the console 14. The X-ray image XP is an example of a radiation image.

The electronic cassette 13 of the present embodiment is not a synchronous type cassette that starts an operation in response to receiving a control signal from the console 14, but is an asynchronous type (synchronous free type) cassette that detects X-rays emitted from the X-ray source 11 and automatically starts operation control. Thus, the electronic cassette 13 has an irradiation start detection function for detecting that irradiation of X-rays has started by detecting the X-rays applied from the X-ray source 11. In a case where the start of X-ray irradiation is detected, the electronic cassette 13 wirelessly transmits an irradiation start detection signal SI to the console 14. The irradiation start detection signal SI is an example of a timing signal according to the technique of the present disclosure.

The X-ray source 11 is suspended vertically downward from a ceiling 2 of an imaging room. The X-ray source 11 is held by a suspension holding mechanism 17. The suspension holding mechanism 17 is attached to the ceiling 2 via a horizontal movement mechanism 18. The suspension holding mechanism 17 holds the X-ray source 11 in a vertical direction (±Z direction) to be able to be moved up and down. The horizontal movement mechanism 18 movably holds the suspension holding mechanism 17 in an X-ray irradiation axis direction (±X direction) and a direction (±Y direction) orthogonal to the X-ray irradiation axis direction of the X-ray source 11.

A motor (not shown) is provided in each of the suspension holding mechanism 17 and the horizontal movement mechanism 18, and it is possible to move the X-ray source 11 manually or electrically in each direction. Operations of the suspension holding mechanism 17 and the horizontal movement mechanism 18 are controlled by the control unit 12C. Whether to move the X-ray source 11 manually or electrically may be selected by using the touch panel 12A. By moving the X-ray source 11, a position of the irradiation field RF can be adjusted.

The optical camera 15 is an optical digital camera configured to include a complementary metal oxide semiconductor (CMOS) type image sensor or a charge coupled device (CCD) type image sensor, and performing imaging on the basis of visible light as an example. The optical camera 15 enables still image capturing and motion picture capturing. The optical camera 15 is an example of a motion picture capturing device according to the technique of the present disclosure.

An optical axis of the optical camera 15 is parallel to the irradiation axis of X-rays passing through the center of the irradiation field RF. The optical camera 15 generates an optical image by optically imaging a region including the irradiation field RF. The optical image is an image indicating the imaging site of the subject H located in the irradiation field RF. The optical image is, for example, a color still image or motion picture.

The optical camera 15 is attached to an outer peripheral portion of the X-ray source 11. The optical camera 15 does not have to be attached to the outer peripheral portion of the X-ray source 11, or may be built in the X-ray source 11. In the optical camera 15, an objective lens and an imaging element may be configured separately. In this case, the objective lens may be disposed on the outer peripheral portion of the X-ray source 11 and the imaging element may be built in a portion other than the X-ray source 11 (for example, an arm supporting the X-ray source 11).

The optical camera 15 is connected to the console 14 by wire or wirelessly. The console 14 functions as an imaging control device to control an imaging operation of the optical camera 15. The console 14 causes the optical camera 15 to capture a still image in conjunction with the irradiation start detection signal SI transmitted from the electronic cassette 13, and also to capture a motion picture during an imaging preparation period before the start of the X-ray imaging. For example, the console 14 is installed in an operation room adjacent to the imaging room in which the X-ray source 11 is installed.

In a case where the irradiation start detection signal SI is received from the electronic cassette 13, the console 14 transmits a still image capturing command signal to the optical camera 15. The optical camera 15 captures a still image of a region including the irradiation field RF in response to the still image capturing command signal input from the console 14. An optical image (hereinafter, referred to as a still image SP) obtained through this still image capturing is transmitted to the console 14.

The console 14 transmits a motion picture capturing start signal to the optical camera 15 in a case where an operation of starting imaging preparation is performed by the technician RG. The optical camera 15 starts to capture a motion picture of a region including the irradiation field RF in response to the motion picture capturing start signal input from the console 14. An optical image (hereinafter, referred to as a motion picture MP) obtained through this motion picture capturing is transmitted to the console 14 as a so-called live view image in real time at the time of motion picture capturing.

The console 14 is connected to a radiology information system (RIS), a picture archiving and communication system (PACS), and an imaging failure management system 19 provided in the X-ray imaging system 10 via the network N. The console 14 has a function of performing X-ray imaging by an operation of the technician RG on the basis of an imaging order, various types of information, and the like acquired from the RIS. The console 14 has a function of transmitting the X-ray image XP received from the electronic cassette 13 to the PACS after the X-ray imaging.

The console 14 has a function of transmitting the X-ray image XP in which it is determined by the technician RG that an imaging failure has occurred to the imaging failure management system 19 after the X-ray imaging. The imaging failure management system 19 collects the X-ray image XP in which it is determined that an imaging failure has occurred and analyzes a cause of the imaging failure.

Figure 2:
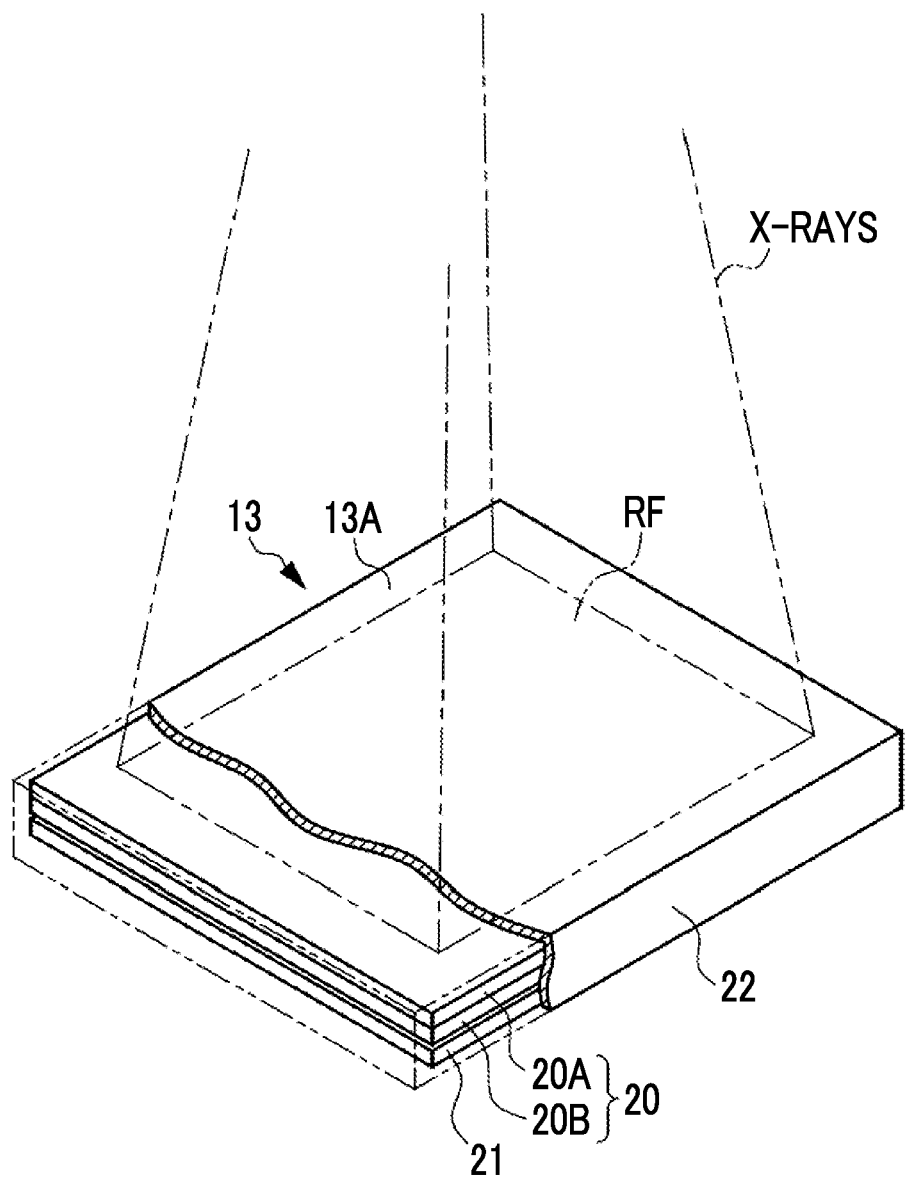
FIG. 2 is an external perspective view of an electronic cassette.

FIG. 2 shows a configuration of the electronic cassette 13. The electronic cassette 13 includes a sensor panel 20, a circuit unit 21, and a rectangular parallelepiped-shaped portable casing 22 that accommodates the sensor panel 20 and the circuit unit 21. The casing 22 has a size conforming to the international standard International Organization for Standardization (ISO) 4090:2001, which is substantially the same as that of, for example, a film cassette, an imaging plate (IP) cassette, or a computed radiography (CR) cassette.

The electronic cassette 13 is positioned in a posture in which the X-ray incident surface 13A that is an upper surface of the casing 22 faces the X-ray source 11, and the X-ray incident surface 13A is irradiated with X-rays. Although not shown, the casing 22 is also provided with a switch for switching between turning-on and turning-off of a main power source, and an indicator for reporting an operation state of the electronic cassette 13 such as a remaining battery usage time or an imaging ready state.

The sensor panel 20 is configured with a scintillator 20A and a light detection substrate 20B. The scintillator 20A and the light detection substrate 20B are laminated in the order of the scintillator 20A and the light detection substrate 20B when viewed from the X-ray incident surface 13A side. The scintillator 20A has phosphors such as CsI: Tl (thallium-activated cesium iodide) or GOS ($Gd_2O_2S$: Tb, terbium-activated gadolinium oxysulfide), and converts X-rays incident via the X-ray incident surface 13A into visible light and emits the visible light. A sensor panel in which the light detection substrate 20B and the scintillator 20A are laminated in this order when viewed from the X-ray incident surface 13A side may be used. A direct conversion type sensor panel that directly converts X-rays into signal charge with a photoconductor such as amorphous selenium may be used.

The light detection substrate 20B detects the visible light emitted from the scintillator 20A and converts the visible light into electric charge. The circuit unit 21 controls the drive of the light detection substrate 20B and generates the X-ray image XP on the basis of the electric charge output from the light detection substrate 20B.

Figure 3:
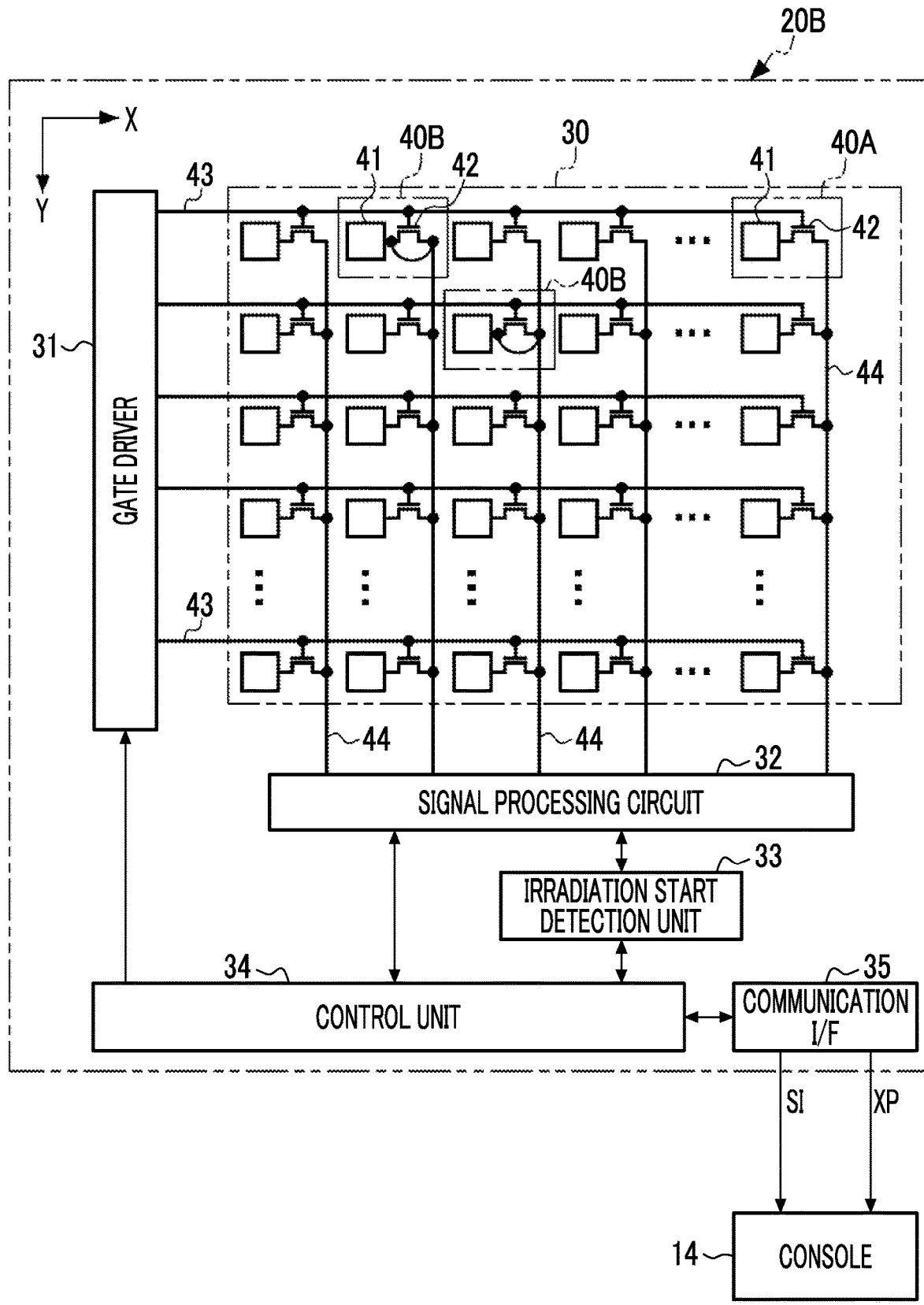
FIG. 3 is a diagram showing a configuration of a light detection substrate.

FIG. 3 shows the configuration of the light detection substrate 20B. The light detection substrate 20B includes a pixel region 30, a gate driver 31, a signal processing circuit 32, an irradiation start detection unit 33, a control unit 34, and a communication interface (I/F) 35.

The pixel region 30 has a plurality of normal pixels 40A arranged in a matrix shape along the X and Y directions orthogonal to each other. The normal pixels 40A are pixels used to detect X-rays and generate the X-ray image XP. The pixel region 30 is provided with detection pixels 40B in addition to the normal pixels 40A. The detection pixels 40B are pixels used to detect the start of irradiation for detecting the start of irradiation of X-rays.

The normal pixel 40A has a photoelectric conversion unit 41 that generates and stores electric charge through photoelectric conversion of visible light converted by the scintillator, and a TFT 42 as a switching element. The photoelectric conversion unit 41 has, for example, a p-intrinsic-n (PIN) type semiconductor layer, an upper electrode disposed on an upper side of the semiconductor layer, and a lower electrode disposed on a lower side of the semiconductor layer. A bias voltage is applied to the upper electrode. The lower electrode is connected to the thin film transistor (TFT) 42.

The detection pixel 40B has a photoelectric conversion unit 41 and a TFT 42, similarly to the normal pixel 40A. However, in the detection pixel 40B, the source electrode and the drain electrode of the TFT 42 are short-circuited to each other. Hereinafter, in a case where it is not necessary to distinguish between the normal pixel 40A and the detection pixel 40B, the pixels will be simply referred to as the pixels 40.

The pixel region 30 has a plurality of scanning lines 43 extending in the X direction and a plurality of signal lines 44 extending in the Y direction. The scanning lines 43 and the signal lines 44 are wired in a grid pattern. The pixels 40 are respectively connected to intersections between the scanning lines 43 and the signal lines 44. Specifically, in the pixel 40, the gate electrode of the TFT 42 is connected to the scanning line 43, and the source electrode of the TFT 42 is connected to the signal line 44. The drain electrode of the TFT 42 is connected to the photoelectric conversion unit 41.

Each scanning line 43 is commonly connected to the pixels 40 for one pixel row. Each signal line 44 is commonly connected to pixels 40 for one pixel column. Each scanning line 43 is connected to the gate driver 31. Each signal line 44 is connected to the signal processing circuit 32.

The gate driver 31 sequentially supplies a gate pulse as a scanning signal to each scanning line 43. The gate pulse supplied to the scanning line 43 is applied to the gate electrode of the TFT 42 included in the pixel 40 connected to the scanning line 43.

The electric charge stored in the photoelectric conversion unit 41 of the normal pixel 40A is output to the signal line 44 in a case where the TFT 42 is turned on. Since the source electrode and the drain electrode of the TFT 42 are short-circuited to each other in the detection pixel 40B, the electric charge generated in the photoelectric conversion unit 41 of the detection pixel 40B is output to the signal line 44 regardless of a switching state of the TFT 42.

The signal processing circuit 32 includes an integrator as a charge amplifier, a correlated double sampling (CDS) circuit, and an analog/digital (A/D) converter. The signal processing circuit 32 integrates the electric charge input from each pixel 40 via the signal line 44 by using the integrator, and then performs correlated double sampling by using the CDS circuit. The signal processing circuit 32 converts a pixel signal from which a reset noise component has been removed through the correlated double sampling into a digital signal by using the A/D converter.

The signal processing circuit 32 generates the X-ray image XP on the basis of pixel signals for one frame read out from the respective normal pixels 40A in the pixel region 30.

Figure 4:
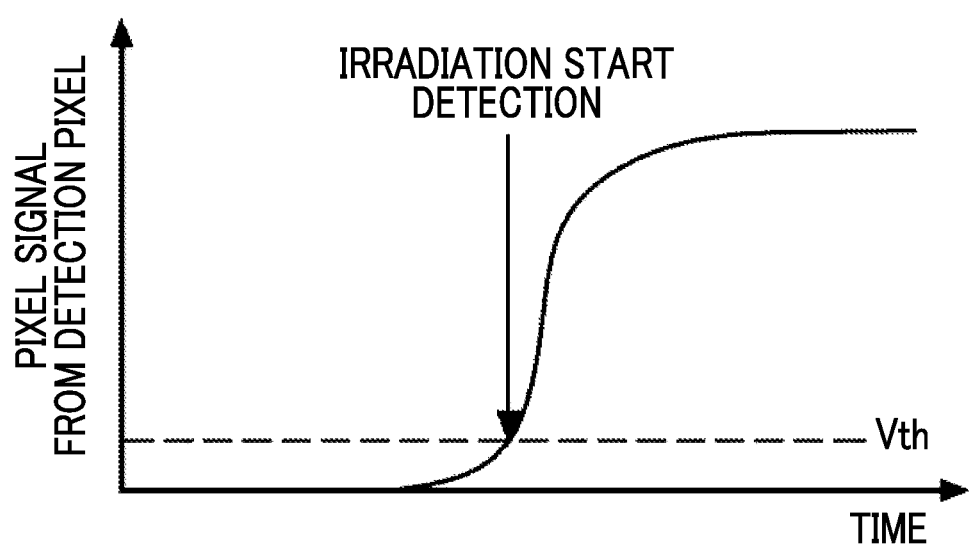
FIG. 4 is a graph for describing irradiation start detection.

The irradiation start detection unit 33 detects the start of X-ray irradiation on the basis of the pixel signal output from the detection pixel 40B via the signal processing circuit 32. The irradiation start detection unit 33 monitors the pixel signal output from the detection pixel 40B. As shown in FIG. 4, the irradiation start detection unit 33 determines that X-ray irradiation has started in a case where the pixel signal output from the detection pixel 40B exceeds a threshold value Vth, and outputs the irradiation start detection signal SI.

For example, the irradiation start detection unit 33 performs irradiation start detection on the basis of the maximum value of the pixel signals output from the plurality of detection pixels 40B. The irradiation start detection unit 33 may perform irradiation start detection on the basis of an average value, a total value, or the like instead of the maximum value. The irradiation start detection unit 33 may perform irradiation start detection on the basis of a temporal change rate of the pixel signal.

The control unit 34 is configured with a microcomputer, and includes a central processing unit (CPU), a memory, and a storage device. The control unit 34 performs control for X-ray image capturing by the CPU executing a program stored in the memory. The control unit 34 controls each constituent of the gate driver 31, the signal processing circuit 32, the irradiation start detection unit 33, and the communication I/F 35.

In a case where the irradiation start detection unit 33 detects the start of X-ray irradiation, the control unit 34 controls the gate driver 31 and the signal processing circuit 32 to perform an operation of resetting the electric charge stored in the normal pixel 40A. Specifically, the control unit 34 supplies a gate pulse from the gate driver 31 to each scanning line 43 such that the stored electric charge of each normal pixel 40A is output to the signal line 44 and the electric charge is discarded in the signal processing circuit 32. After the reset operation is finished, the control unit 34 turns off all TFTs 42 to bring the normal pixel 40A into a charge storage state.

After the normal pixel 40A is brought into the charge storage state and then a predetermined X-ray irradiation time elapses, the control unit 34 controls the gate driver 31, and reads out the pixel signal from the normal pixel 40A to the signal processing circuit 32 to generate the X-ray image XP.

In a case where the irradiation start detection unit 33 detects the start of X-ray irradiation, the control unit 34 outputs the irradiation start detection signal SI to the console 14 via the communication I/F 35. The control unit 34 outputs the X-ray image XP to the console 14 via the communication I/F 35 after the X-ray image XP is generated by the signal processing circuit 32.

Figure 5:
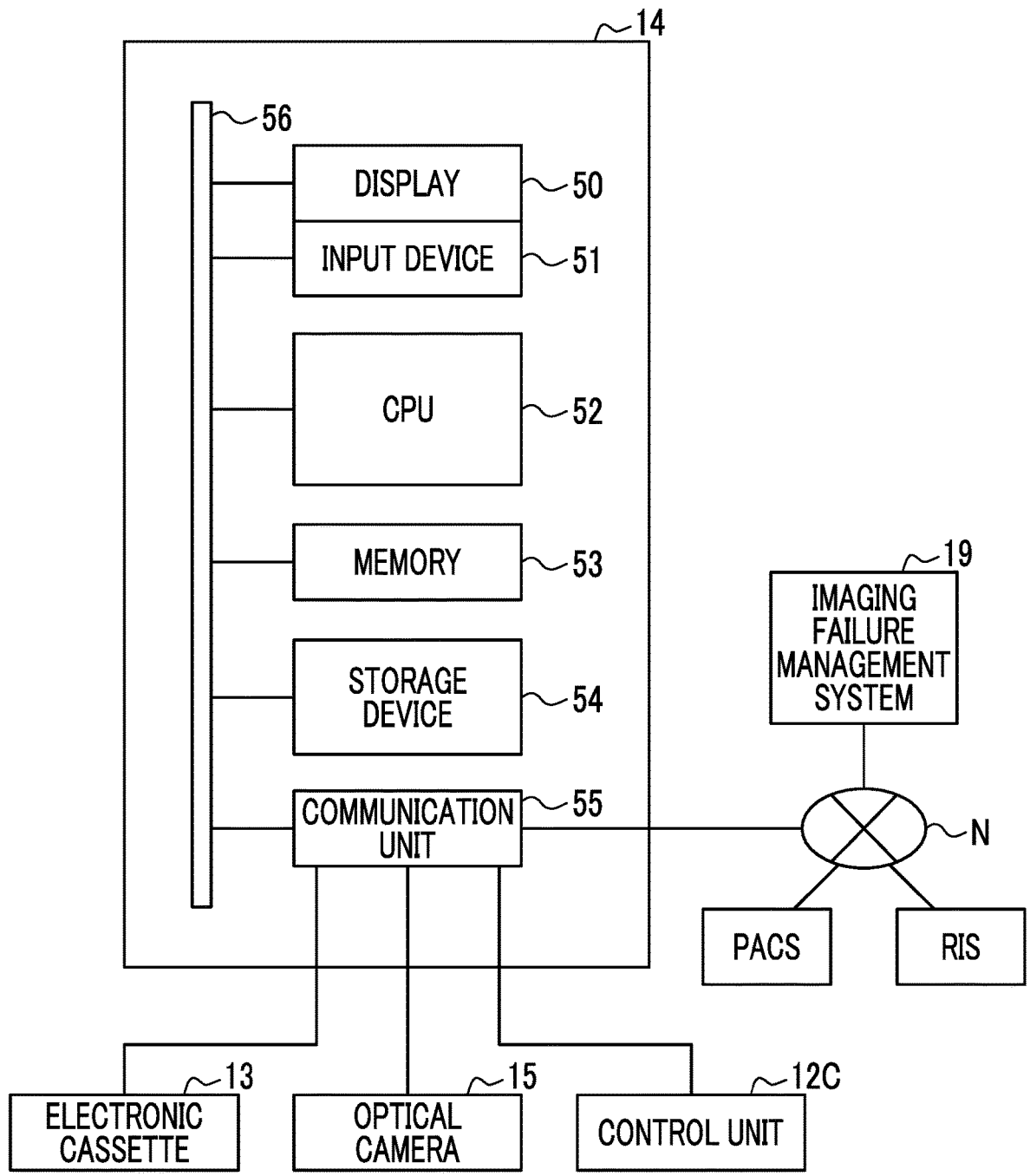
FIG. 5 is a block diagram showing a configuration of a console.

In FIG. 5, the console 14 has a display 50, an input device 51, a CPU 52, a memory 53, a storage device 54, and a communication unit 55. These constituents are connected to each other via a data bus 56.

The display 50 is a display unit that displays various operation screens provided with operation functions by a graphical user interface (GUI), the X-ray image XP, and the optical images (the still image SP and the motion picture MP). The input device 51 is an input operation unit including a touch panel, a keyboard, or the like.

The storage device 54 is, for example, a hard disk drive (HDD) array, and is built in the console 14 or externally connected to the console 14. External connection is made via a cables or a network. The storage device 54 stores control programs such as an operating system, various application programs, and various types of data associated with these programs.

The memory 53 is a work memory for the CPU 52 to execute a process. The CPU 52 collectively controls each unit of the console 14 by loading the program stored in the storage device 54 to the memory 53 and executing processes according to the program. The communication unit 55 transmits and receives various types of data such as the X-ray image XP and the optical images (the still image SP and the motion picture MP) to and from the electronic cassette 13 and the optical camera 15. The communication unit 55 communicates with the control unit 12C of the radiation source control device 12.

Figure 6:
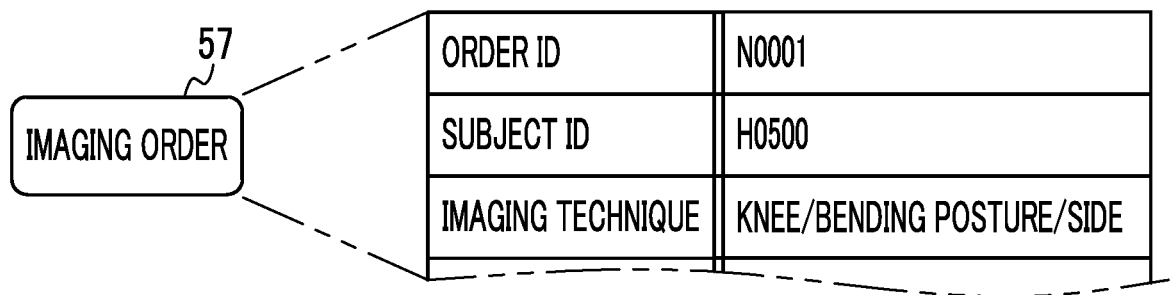
FIG. 6 is a diagram exemplifying an imaging order.

The console 14 receives input of an imaging order 57 shown in FIG. 6. The imaging order 57 is information for instructing the technician RG to perform X-ray imaging, for example, from an imaging requester in a clinical department. The imaging order 57 is delivered from the RIS to the console 14.

The imaging order 57 has items such as an order identification data (ID), a subject ID, and an imaging technique. The order ID is a symbol or number that identifies each imaging order 57, and is automatically assigned by the RIS. In the item of subject ID, a subject ID of the subject H who is an imaging target is written. The subject ID is a symbol or a number that identifies each subject H.

The imaging technique is information regarding an imaging site of the subject H and a posture and an orientation of the imaging site. In addition to the knees exemplified in FIG. 1, the imaging site includes the head, the cervical spine, the chest, the abdomen, hands, fingers, elbows, and the like. The posture is a posture of the subject H such as a standing posture, a lying posture, or a sitting posture. The orientation is an orientation of the subject H with respect to the X-ray source 11, such as the front, the side, or the back. In addition to these items, the imaging order 57 includes items of subject information (patient information) such as the name, gender, age, height, and weight of the subject H.

Figure 7:
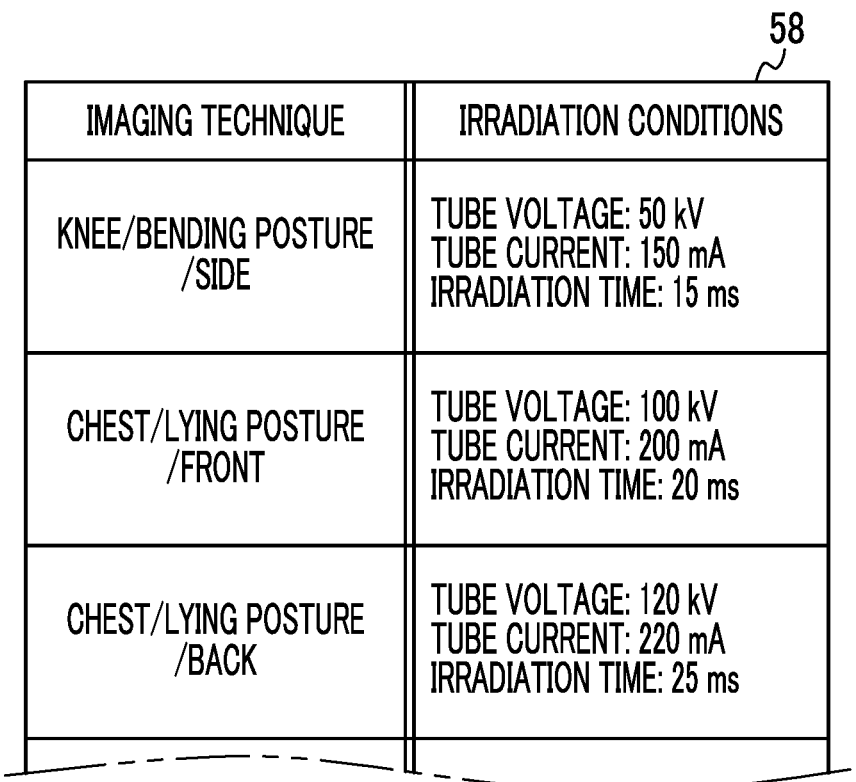
FIG. 7 is a diagram exemplifying a condition table.

The condition table 58 shown in FIG. 7 is stored in the storage device 54 of the console 14. Irradiation conditions corresponding to each imaging technique are associated and registered in the condition table 58.

The console 14 displays an imaging order list that lists the details of the imaging order 57 shown in FIG. 6 on the display 50 through an operation of the technician RG. The technician RG may view the imaging order list and check the details of the imaging order 57. The console 14 displays the details of the condition table 58 shown in FIG. 7 on the display 50. The technician RG may select and set irradiation conditions that match the imaging technique designated in the imaging order 57.

The console 14 wirelessly transmits condition setting signals including various types of information such as irradiation conditions set by the technician RG, an order ID, and a console ID as console identification information to the electronic cassette 13.

The console 14 stores the X-ray image XP received from the electronic cassette 13 in the storage device 54 that is a storage unit, for example, as an image file in a format conforming to the Digital Imaging and Communication in Medicine (DICOM) standard. In the image file, the X-ray image XP and accessory information are associated with each other by one image ID. The accessory information includes an order ID, a subject ID, patient information, an imaging technique, irradiation conditions, and the like.

Figure 8:
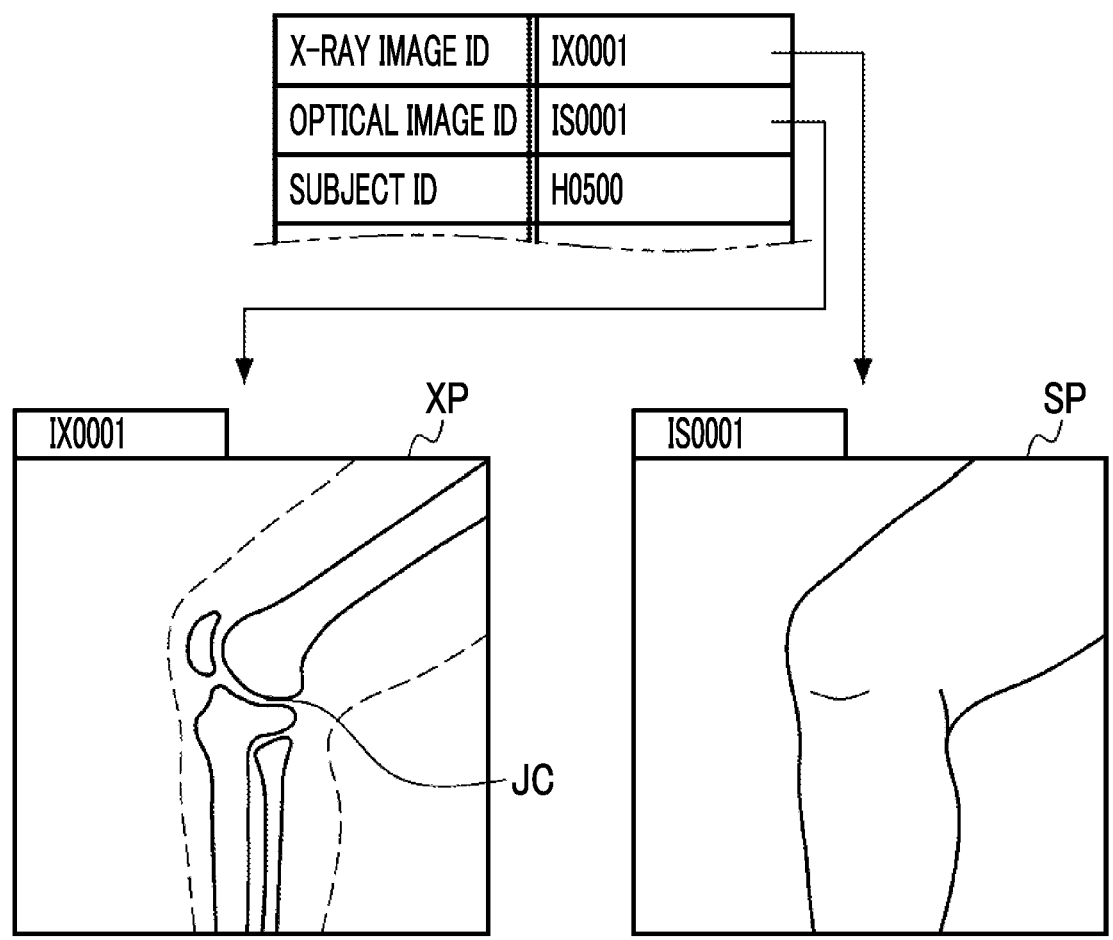
FIG. 8 is a diagram exemplifying an X-ray image and still image that are associated with each other.

The still image SP obtained by the optical camera 15 capturing a still image in conjunction with the irradiation start detection signal SI is added with an image ID (optical image ID) associated with an image ID (X-ray image ID) of the X-ray image XP obtained through the X-ray imaging. As shown in FIG. 8, the X-ray image XP and the still image SP obtained when X-ray imaging is performed once are stored in the storage device 54 in association with the X-ray image ID and the optical image ID.

In a case where the imaging technique is "knee/bending posture/side", a doctor mainly makes a diagnosis of the joint cavity JC of the knee on the basis of the X-ray image XP. Thus, it is necessary that the joint cavity JC is clearly depicted in the X-ray image XP.

Figure 9:
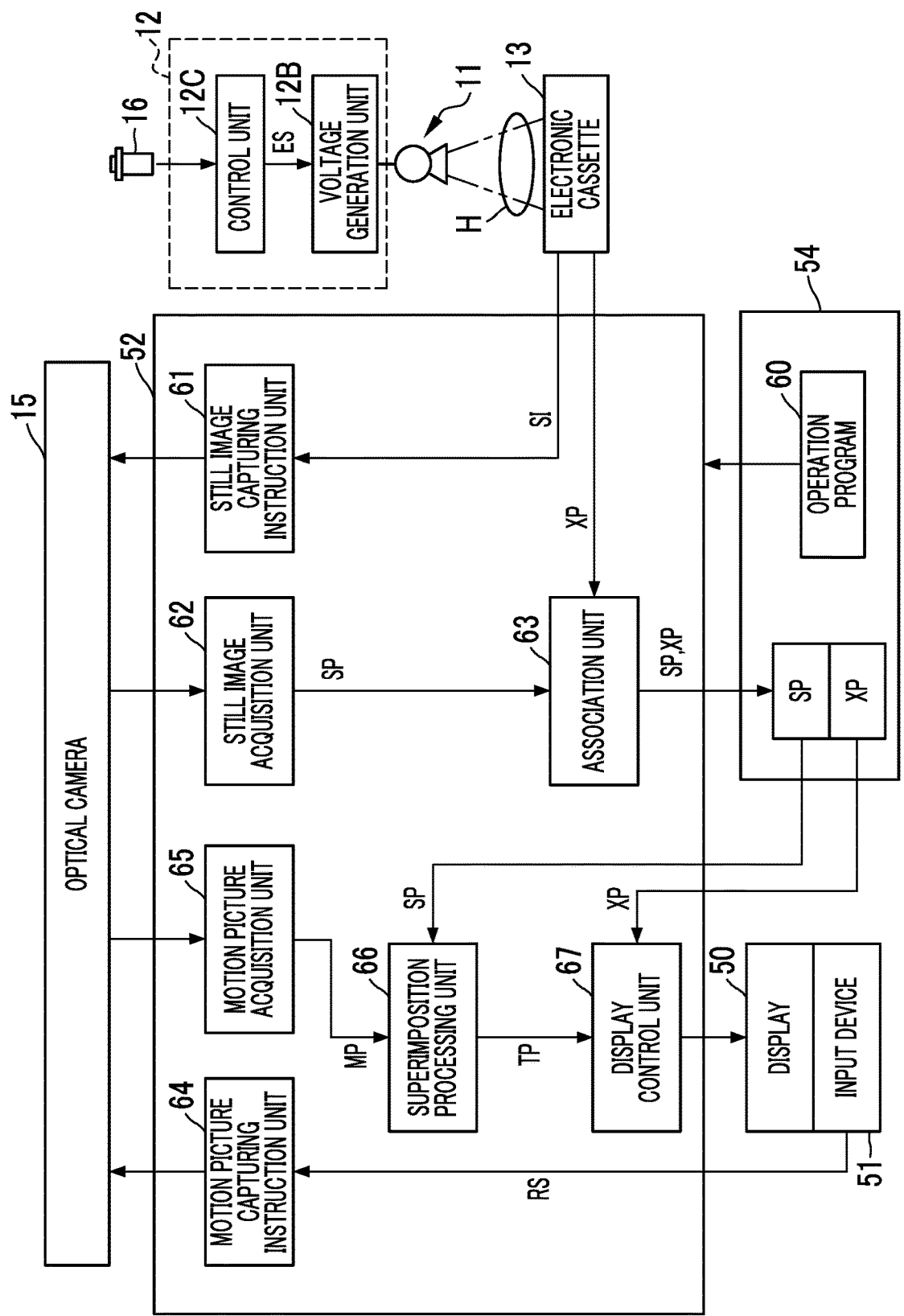
FIG. 9 is a block diagram showing each functional unit configured in a CPU.

FIG. 9 shows various functions provided in the CPU 52. The storage device 54 stores an operation program 60. Although not shown, the condition table 58 shown in FIG. 7 is also stored in the storage device 54. A plurality of functional units are configured in the CPU 52 by executing the operation program 60.

The operation program 60 causes the CPU 52 to function as a still image capturing instruction unit 61, a still image acquisition unit 62, an association unit 63, a motion picture capturing instruction unit 64, a motion picture acquisition unit 65, a superimposition processing unit 66, and a display control unit 67.

The still image capturing instruction unit 61 receives the irradiation start detection signal SI transmitted from the electronic cassette 13 via the communication unit 55 in response to the irradiation switch 16 being pressed and thus irradiation with X-rays from the X-ray source 11 to the electronic cassette 13 being started. The still image capturing instruction unit 61 instructs the optical camera 15 to execute still image capturing in response to receiving the irradiation start detection signal SI from the electronic cassette 13.

The still image acquisition unit 62 acquires the still image SP generated by the optical camera 15 capturing a still image. The still image SP acquired by the still image acquisition unit 62 is input to the association unit 63. The association unit 63 receives the X-ray image XP detected by the electronic cassette 13 via the communication unit 55 on the basis of the X-rays applied from the X-ray source 11 in response to the irradiation switch 16 being pressed.

The association unit 63 stores the still image SP input to the still image acquisition unit 62 and the X-ray image XP input from the electronic cassette 13 in the storage device 54 in association with each other as shown in FIG. 8. The association unit 63 associates the associated still image SP and the X-ray image XP with the above accessory information (refer to FIG. 8) such as patient information, and stores the images in the storage device 54.

The motion picture capturing instruction unit 64 transmits a motion picture capturing start signal for instructing the optical camera 15 to start motion picture capturing in response to input of a reimaging preparation start signal RS from the input device 51. The technician RG checks the X-ray image XP acquired through the X-ray imaging, and in a case where it is determined that there is an imaging failure, the technician RG operates the input device 51 to cause the imaging support device to transition to a reimaging preparation mode. In a case where the imaging technique is "knee/bending posture/side", the technician RG determines that there is an imaging failure in a case where, for example, the joint cavity JC of the knee is not clearly depicted in the X-ray image XP.

The motion picture acquisition unit 65 acquires, in real time for each frame, the motion picture MP generated by the optical camera 15 capturing a motion picture. The motion picture acquisition unit 65 acquires an optical image for each frame and outputs the motion picture MP formed of a plurality of acquired frames. The motion picture MP acquired by the motion picture acquisition unit 65 is input to the superimposition processing unit 66 for each frame.

Figure 10:
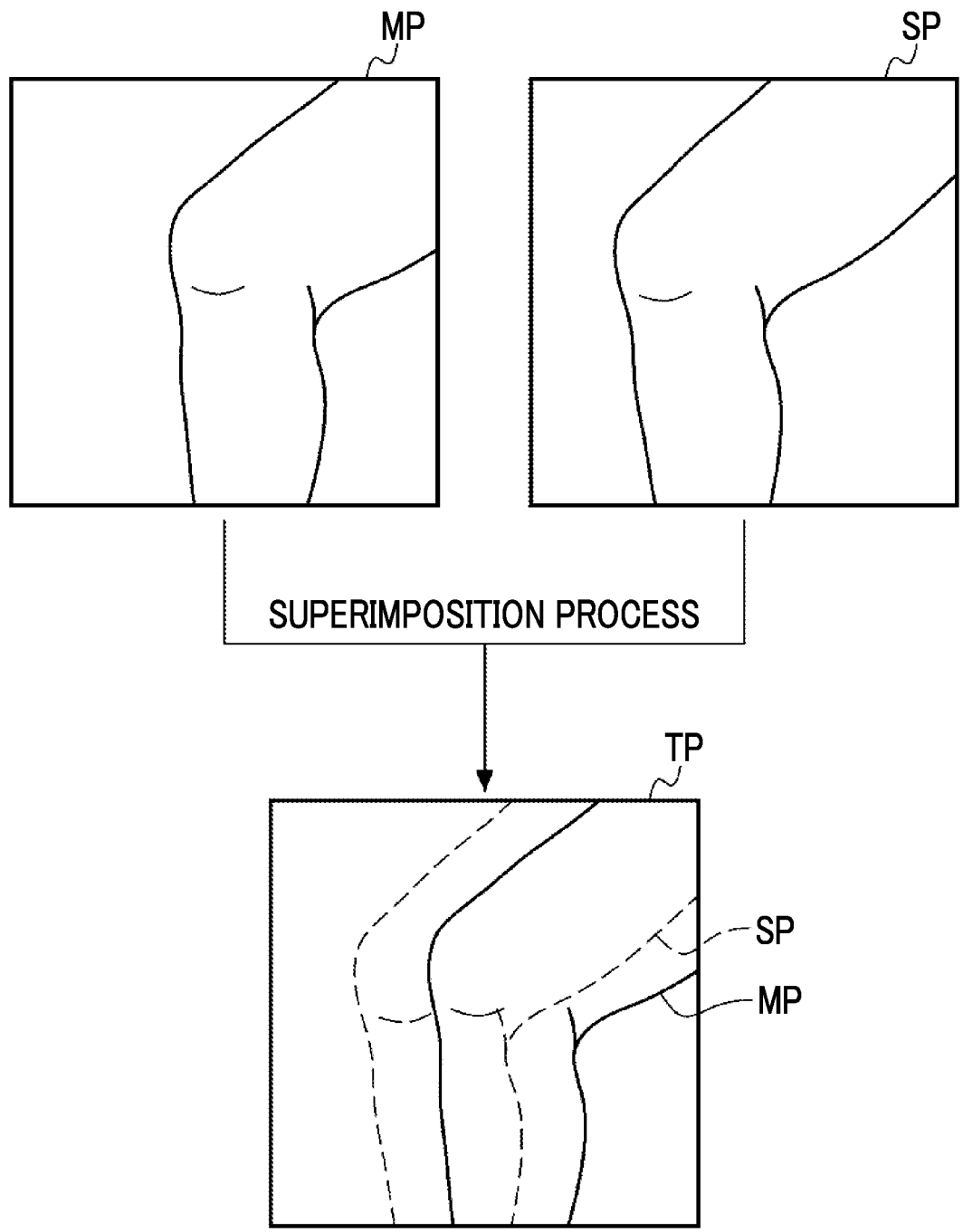
FIG. 10 is a diagram exemplifying a superimposition process.

The superimposition processing unit 66 acquires the still image SP stored in the storage device 54, and superimposes the still image SP on each frame of the motion picture MP as shown in FIG. 10. The superimposition processing unit 66 inputs a superimposition image TP generated by superimposing the motion picture MP and the still image SP to the display control unit 67 for each frame. The display control unit 67 displays the superimposition image TP on the display 50 for each frame. That is, the display control unit 67 superimposes the still image SP on the motion picture MP and displays the superimposition image on the display 50 in real time.

The still image SP in the superimposition image TP is associated with the X-ray image XP in which the technician RG has determined that there is an imaging failure, and indicates a position of the subject H at the time of imaging failure. The motion picture MP in the superimposition image TP indicates the current position of the subject H during reimaging preparation. Therefore, the technician RG can check the current position of the subject H with respect to the time of imaging failure by checking the superimposition image TP displayed in real time on the display 50.

The motion picture capturing of the optical camera 15 is finished in response to receiving an execution instruction for still image capturing from the still image capturing instruction unit 61 described above. After the motion picture capturing is finished, the motion picture MP is discarded without being stored in the storage device 54. This is for the purpose of preventing the motion picture MP from being stored in the storage device 54, that is, privacy protection, in a case where unnecessary information is captured in the motion picture MP during imaging preparation. The still image acquisition unit 62 may acquire one frame of the motion picture MP as the still image SP.

The display control unit 67 causes the display 50 to display a console screen that allows the technician RG to perform various operations such as selection of the imaging order 57 using the input device 51. The display control unit 67 displays the X-ray image XP or the superimposition image TP on the console screen.

Figure 11:
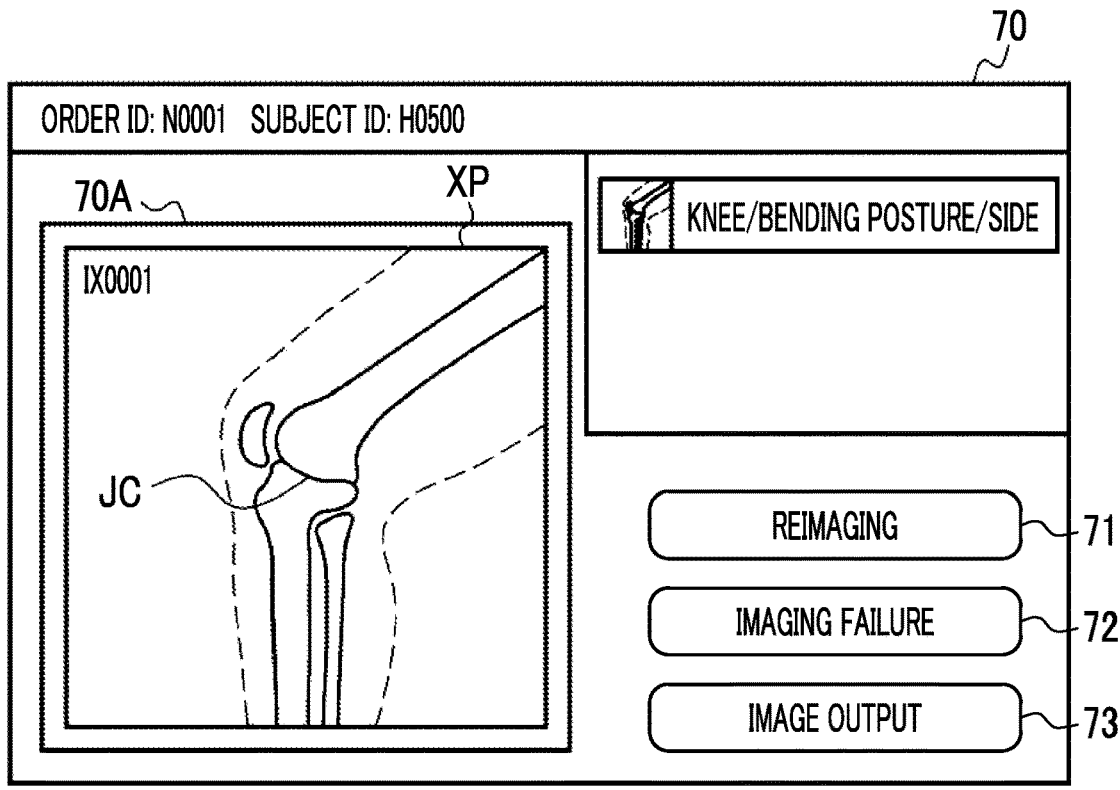
FIG. 11 is a diagram showing a display example of a console screen after X-ray imaging.

FIG. 11 shows an example of a console screen displayed on the display 50 by the display control unit 67. As shown in FIG. 11, a console screen 70 is provided with an image display region 70A for displaying an image such as the X-ray image XP or the superimposition image TP.

On the console screen 70, a first operation button 71 for performing reimaging, a second operation button 72 for outputting the X-ray image XP in which the occurrence of an imaging failure is determined to the imaging failure management system 19, and a third operation button 73 for outputting the X-ray image XP to the PACS are displayed. The first operation button 71, the second operation button 72, and the third operation button 73 are operated by a touch panel formed on the screen of the display 50.

FIG. 11 shows a display example of the console screen 70 after X-ray imaging. In the example shown in FIG. 11, the X-ray image XP obtained through X-ray imaging is displayed in the image display region 70A. In a case where the technician RG determines that the X-ray image XP is not an image suitable for diagnosis and reimaging is necessary (that is, imaging failure), the technician RG may press the second operation button 72 to transmit the X-ray image XP to the imaging failure management system 19. In this case, the technician RG may cause the X-ray imaging system 10 to start an imaging preparation operation for reimaging by pressing the first operation button 71.

On the other hand, in a case where the technician RG determines that the X-ray image XP is an image suitable for diagnosis and reimaging is unnecessary, the technician RG may press the third operation button 73 to transmit the X-ray image XP to the PACS.

In a case where the X-ray image XP is transmitted to the outside such as the imaging failure management system 19 or the PACS, the console 14 preferably outputs a file (refer to FIG. 8) in which accessory information such as patient information is associated with the still image SP and the X-ray image XP associated by the association unit 63.

Figure 12:
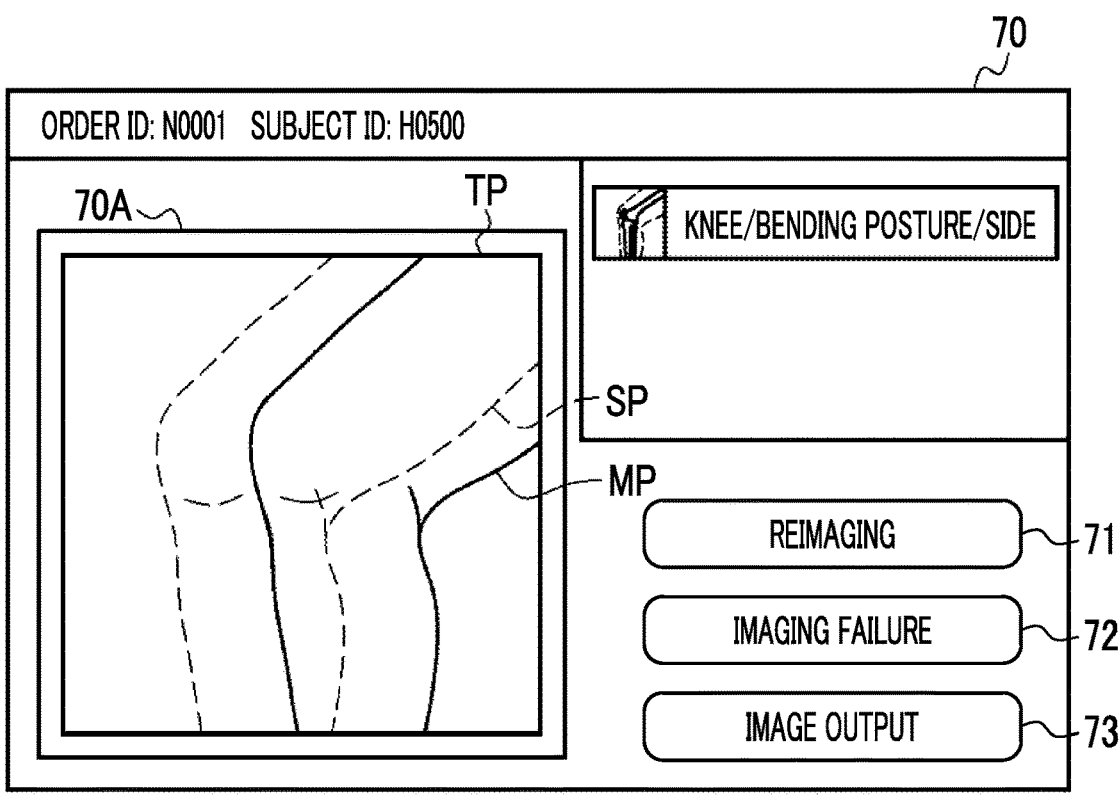
FIG. 12 is a diagram showing a display example of a console screen in an imaging preparation operation for reimaging.

FIG. 12 shows a display example of the console screen 70 in the imaging preparation operation for reimaging. In the example shown in FIG. 12, the superimposition image TP in which the still image SP is superimposed on the motion picture MP is displayed in the image display region 70A. The still image SP indicates a position of the subject H at the time of imaging failure. The motion picture MP indicates the current position of the subject H in an imaging preparation operation. Consequently, the technician RG can position the subject H while referring to the still image SP indicating the position of the subject H at the time of imaging failure.

Figure 13:
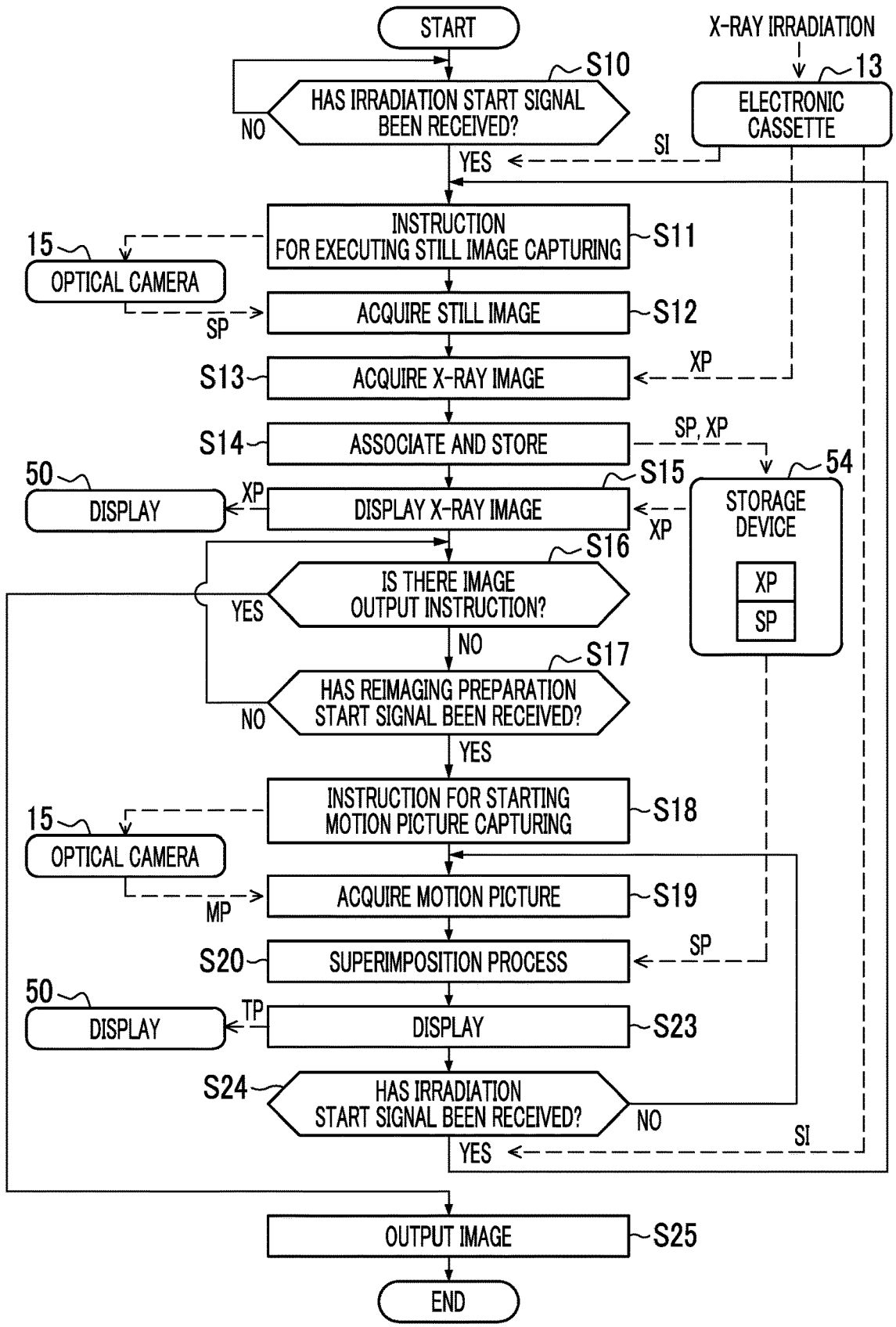
FIG. 13 is a flowchart for describing a process procedure of the CPU.

Next, an operation of the imaging support device having the above configuration will be described with reference to a flowchart of FIG. 13. First, prior to imaging, the technician RG checks details of the imaging order 57 on the display 50, and sets irradiation conditions by using the input device 51 and the touch panel 12A. Next, the technician RG positions the X-ray source 11, the electronic cassette 13, and the subject H according to an imaging technique included in the imaging order 57. Here, the imaging technique is "knee/bending posture/side". The technician RG bends one leg of the subject H and positions the subject H such that the side of the knee faces the X-ray incident surface 13A of the electronic cassette 13 and the knee is located at the center of the irradiation field RF (refer to FIG. 1).

The still image capturing instruction unit 61 determines whether or not the irradiation start detection signal SI has been received from the electronic cassette 13 (step S10). The irradiation start detection signal SI is a timing signal that is transmitted from the electronic cassette 13 to the console 14 by the irradiation start detection unit 33 of the electronic cassette 13 detecting the start of X-ray irradiation in response to the irradiation switch 16 being pressed by the technician RG and thus irradiation with X-rays from the X-ray source 11 to the electronic cassette 13 being started. The irradiation start detection unit 33 detects the start of X-ray irradiation, and then the electronic cassette 13 detects the X-ray image XP of the subject H on the basis of the X-rays transmitted through the subject H.

In a case where the irradiation start detection signal SI has been received (step S10: YES), the still image capturing instruction unit 61 instructs the optical camera 15 to execute still image capturing (step S11). The still image acquisition unit 62 acquires the still image SP generated by the optical camera 15 capturing a still image (step S12). The console 14 acquires the X-ray image XP detected by the electronic cassette 13 (step S13).

Next, the association unit 63 stores the acquired X-ray image XP and the still image SP in the storage device 54 in association with each other (step S14). The display control unit 67 displays the X-ray image XP stored in the storage device 54 in the image display region 70A of the console screen 70 (step S15).

Next, the CPU 52 determines whether or not there has been an instruction for outputting an image by the technician RG pressing the third operation button 73 (step S16). The technician RG checks the X-ray image XP (refer to FIG. 11) displayed in the image display region 70A, and in a case where it is determined that reimaging is unnecessary, the technician RG presses the third operation button 73 to give an instruction for outputting an image. In a case where it is determined that the third operation button 73 is pressed (step S16: YES), the CPU 52 outputs the X-ray image XP stored in the storage device 54 to the PACS (step S25), and finishes the process.

On the other hand, the technician RG checks the X-ray image XP displayed in the image display region 70A, and in a case where it is determined that reimaging is necessary, the technician RG presses the second operation button 72 to give an instruction for transmitting the X-ray image XP to the imaging failure management system 19. Thereafter, the technician RG presses the first operation button 71 to give an instruction for starting preparation for reimaging. In a case where the first operation button 71 is pressed, the input device 51 generates a reimaging preparation start signal RS and transmits the signal to the motion picture capturing instruction unit 64.

In a case where it is determined in step S16 that the third operation button 73 has not been pressed (step S16: NO), the motion picture capturing instruction unit 64 determines whether or not the reimaging preparation start signal RS has been received from the input device 51 (step S17). In a case where the reimaging preparation start signal RS has been received (step S17: YES), the motion picture capturing instruction unit 64 transmits a motion picture capturing start signal to the optical camera 15 (step S18). The motion picture acquisition unit 65 acquires the motion picture MP generated by the optical camera 15 capturing a motion picture for each frame (step S19).

The superimposition processing unit 66 acquires the still image SP stored in the storage device 54, and performs a process of superimposing the still image SP on the frame of the motion picture MP acquired by the motion picture acquisition unit 65 to generate the superimposition image TP (step S20). The display control unit 67 displays the superimposition image TP generated by the superimposition processing unit 66 in the image display region 70A of the console screen 70 (step S23).

The technician RG can position the subject H while referring to the still image SP indicating the position of the subject H at the time of imaging failure by checking the superimposition image TP (refer to FIG. 12) displayed in the image display region 70A. In a case where the positioning of the subject H has been completed, the technician RG presses the irradiation switch 16 to give an instruction for executing X-ray imaging.

In the same manner as in step S10, the still image capturing instruction unit 61 determines whether or not the irradiation start detection signal SI has been received from the electronic cassette 13 (step S24). While the still image capturing instruction unit 61 does not receive the irradiation start detection signal SI (step S24: NO), the process returns to step S19, and the motion picture acquisition unit 65 acquires the next frame of the motion picture MP. Until the irradiation start detection signal SI is received, the processes in steps S19 to S24 are repeatedly executed. Consequently, the superimposition image TP in which the still image SP is superimposed on the motion picture MP is displayed on the image display region 70A in real time.

In a case where the technician RG presses the irradiation switch 16 and thus the still image capturing instruction unit 61 receives the irradiation start detection signal SI (step S24: YES), the still image capturing instruction unit 61 instructs the optical camera 15 to execute still image capturing (step S11). In a case where the instruction for executing still image capturing is received, the optical camera 15 finishes motion picture capturing and performs still image capturing. Thereafter, the same process is executed.

An effect of the imaging support device having the above configuration will be described. After the irradiation switch 16 is pressed by the technician RG, it takes a certain amount of time for the radiation source control device 12 to generate X-rays in the X-ray tube 11A. Therefore, there is a time lag before the start of irradiation after the irradiation switch 16 is pressed. In particular, in a case where the irradiation switch 16 is a two-step switch capable of performing a two-step pressing operation such as half-pressing and full-pressing, the time lag becomes large. In a case where the irradiation switch 16 is a two-step switch, for example, the warm-up of the X-ray tube 11A is started in response to the half-pressing of the irradiation switch 16, and in a case where the irradiation switch 16 is full-pressed after the warm-up is completed, the X-ray tube 11A generates X-rays. Since it takes a certain amount of time to warm up the X-ray tube 11A, the time lag becomes large.

Therefore, in a case where the optical camera 15 executes still image capturing at a timing at which the irradiation switch 16 is pressed, still image capturing is performed before actual X-ray imaging is performed. Therefore, there is a difference between acquisition times of the X-ray image XP and the still image SP associated by the association unit 63 and stored in the storage device 54. In a case where there is a difference between the acquisition times of the X-ray image XP and the still image SP, the still image SP in the superimposition image TP is not an image that accurately represents a position of the subject H at the time of imaging failure, and thus the positioning accuracy of the subject H deteriorates such that there is a possibility that imaging failure will occur again.

In contrast, in the imaging support device having the above configuration, the CPU 52 causes the optical camera 15 to execute still image capturing at a timing at which the irradiation start detection signal SI is received from the electronic cassette 13 instead of a timing at which the irradiation switch 16 is pressed. Consequently, the difference between the acquisition times of the X-ray image XP and the still image SP associated by the association unit 63 is reduced, and the positioning accuracy of the subject H at the time of reimaging is improved. As a result, the possibility that an imaging failure will occur again due to reimaging can be reduced, and an amount of exposure to X-rays of the subject H can be suppressed.

In a case where the technician RG determines the necessity of reimaging by using only the X-ray image XP, there is a possibility that unnecessary reimaging will be performed by erroneously determining the X-ray image XP that does not require reimaging as the occurrence of an imaging failure. Depending on physical characteristics of the subject H and the like, there may be no possibility of improvement even after reimaging. In such a case, unnecessary reimaging may be repeatedly performed. In contrast, in the imaging support device having the above configuration, the X-ray image XP and the still image SP with a less difference between acquisition times thereof are acquired. Thus, by using the still image SP captured at the same time as the X-ray image XP for determination of reimaging, it is possible to more accurately determine the necessity of reimaging.

Hereinafter, an effect of the imaging support device having the above configuration regarding positioning of the subject H will be described with reference to FIGS. 14 and 15. In a case of performing X-ray imaging, depending on imaging sites, even though the technician RG thinks that the subject H is positioned accurately, the actual positioning is not performed properly, and as a result, an imaging failure may occur. For example, in a case of diagnosing a joint of the knee, the joint cavity JC needs to be clearly depicted in the X-ray image XP, but since X-rays are a flux of light that radially diverges from the focal point of the X-ray source 11, an incidence angle of X-rays changes due to a slight misregistration of the joint, and thus the depiction of the joint cavity JC is unclear. In a case where the depiction of the joint cavity JC is unclear, an imaging failure occurs and reimaging is required.

In a case where reimaging is required due to the imaging failure as described above, the technician RG needs to position the subject H again. In a case of adjusting a slight misregistration of the subject H in order to perform reimaging, it is often sufficient to perform fine adjustment on the basis of a position of the subject H at the time of imaging failure.

Figure 14:
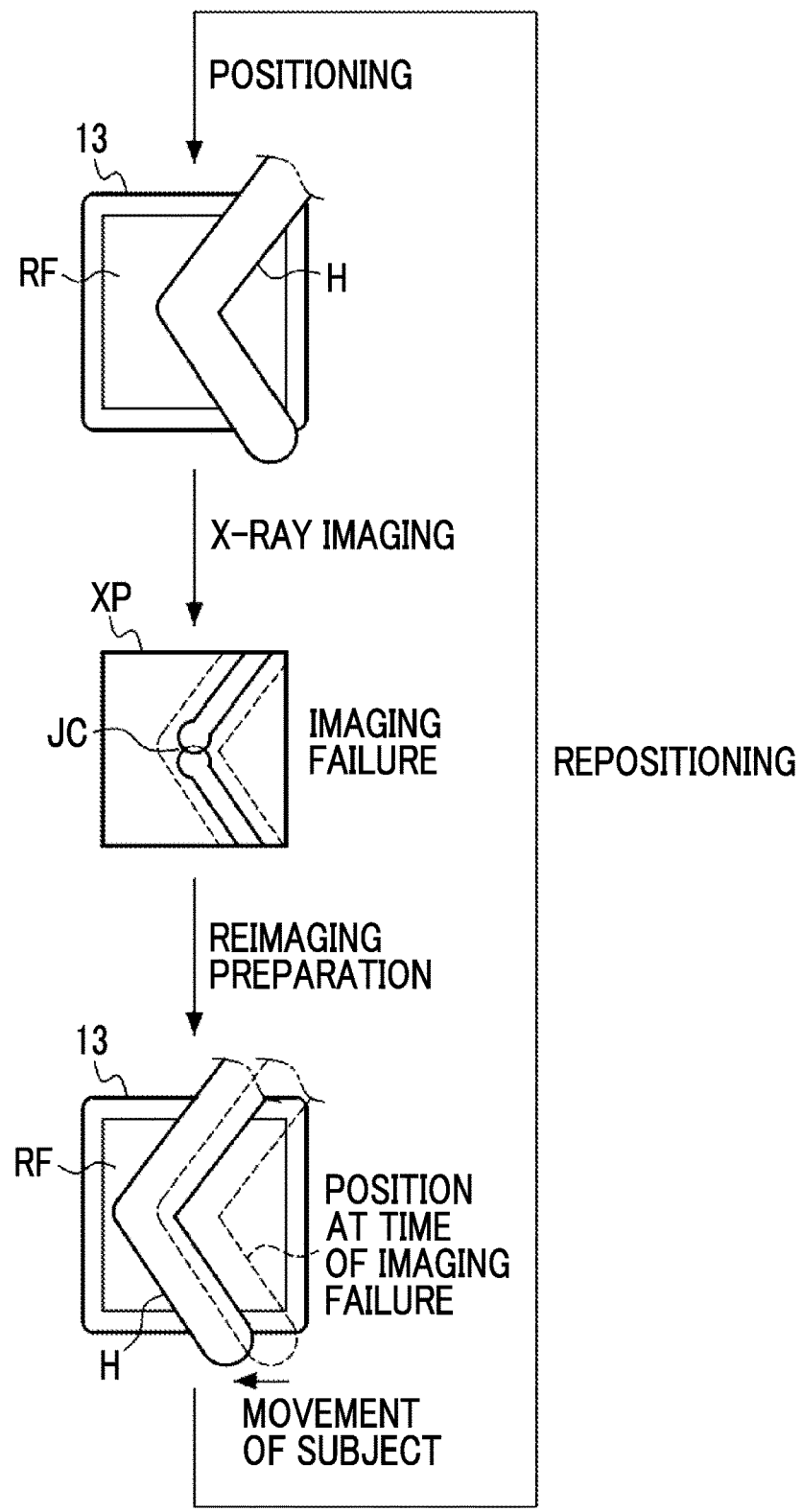
FIG. 14 is a diagram for describing a problem in the related art.

However, as shown in FIG. 14, in a device not having the optical camera of the related art, in a case where the subject H moves significantly from the time of imaging failure, the technician RG cannot accurately ascertain the position of the subject H at the time of imaging failure, and thus cannot perform fine adjustment. In a case where the technician RG repositions the subject H from the beginning, there is a high possibility that the subject H will be positioned to the same position again, and the imaging failure will occur again. As described above, even though the subject H is positioned by using an optical camera or the like before X-ray imaging, in a case where the imaging failure occurs, since the technician RG cannot ascertain the position of the subject H at the time of imaging failure, there is a high possibility that an imaging failure will occur again, and reimaging will be repeated.

Figure 15:
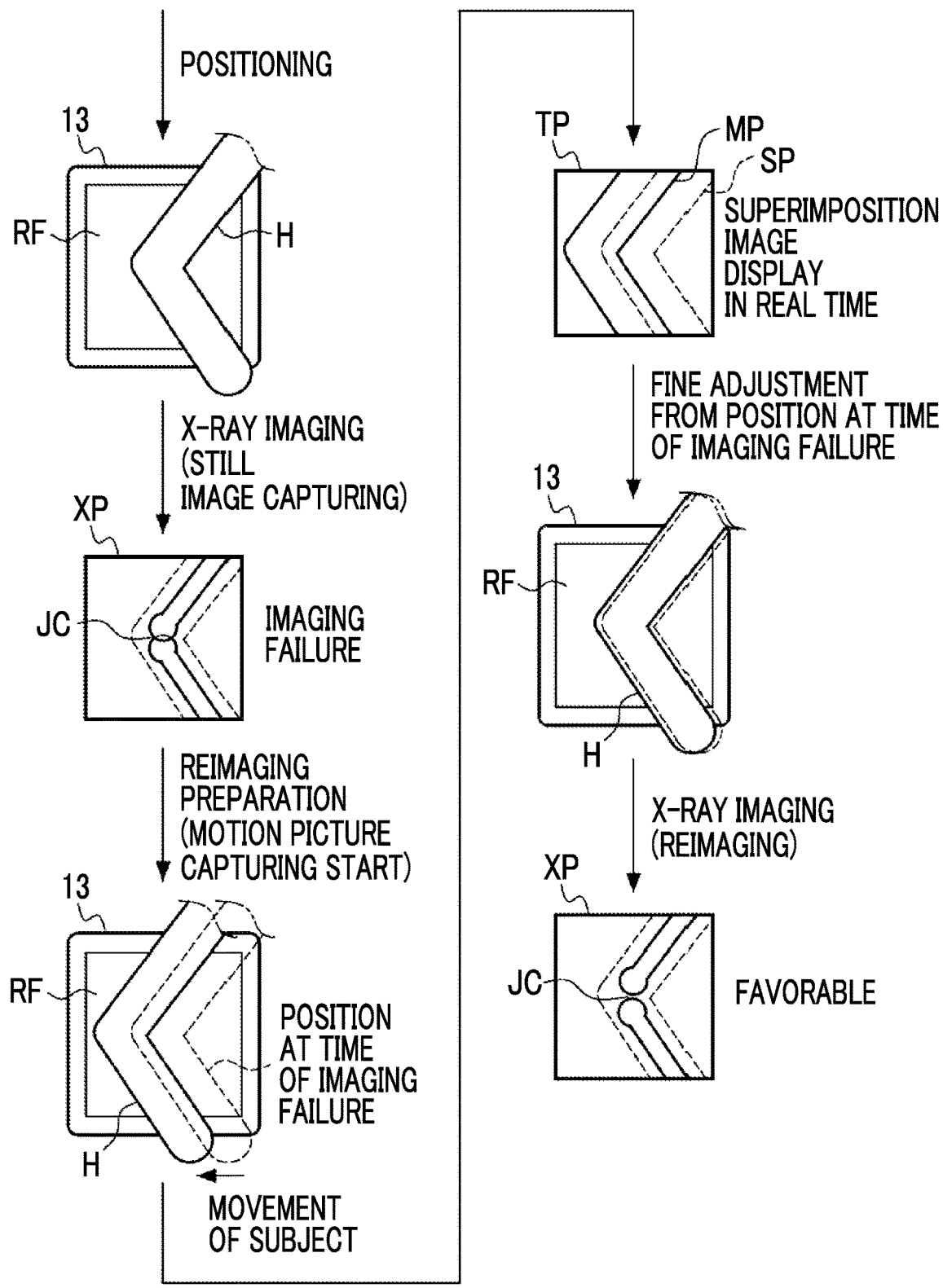
FIG. 15 is a diagram for describing the effect of the technique of the present disclosure.

In contrast, as shown in FIG. 15, in the technique of the present disclosure, since an optical image (still image SP) indicating the subject H is acquired in conjunction with the start of X-ray irradiation, even though the subject H moves significantly from the time of imaging failure, the technician RG can easily ascertain the position of the subject H at the time of imaging failure. Therefore, the technician RG can position the subject H to the position at the time of imaging failure and then finely adjust the position of the subject H from the position at the time of imaging failure on the basis of a reason for the imaging failure or the like. The favorable X-ray image XP can be obtained by finely adjusting the position of the subject H and then performing reimaging. As described above, according to the technique of the present disclosure, it is possible to suppress the repetition of reimaging. As a result, unnecessary exposure of the subject H can be suppressed and the examination time can be reduced.

In the technique of the present disclosure, the superimposition image TP in which the optical image (still image SP) acquired in conjunction with the start of X-ray irradiation and the current optical image (motion picture MP) of the subject H are superimposed is displayed in real time. Even though the subject H moves significantly from the time of the imaging failure, the technician RG can more easily ascertain the position of the subject H at the time of imaging failure on the basis of the still image SP in the superimposition image TP.

Modification Example of First Embodiment

Next, a modification example of the first embodiment of the present disclosure will be described. In the first embodiment, the still image acquisition unit 62 acquires the still image SP obtained by the optical camera 15 receiving an instruction from the still image capturing instruction unit 61 and performing still image capturing. Alternatively, in the present modification example, the still image acquisition unit 62 extracts one frame from the motion picture MP on the basis of the irradiation start detection signal SI transmitted from the electronic cassette 13, and acquires the extracted frame as the still image SP.

Figure 16:
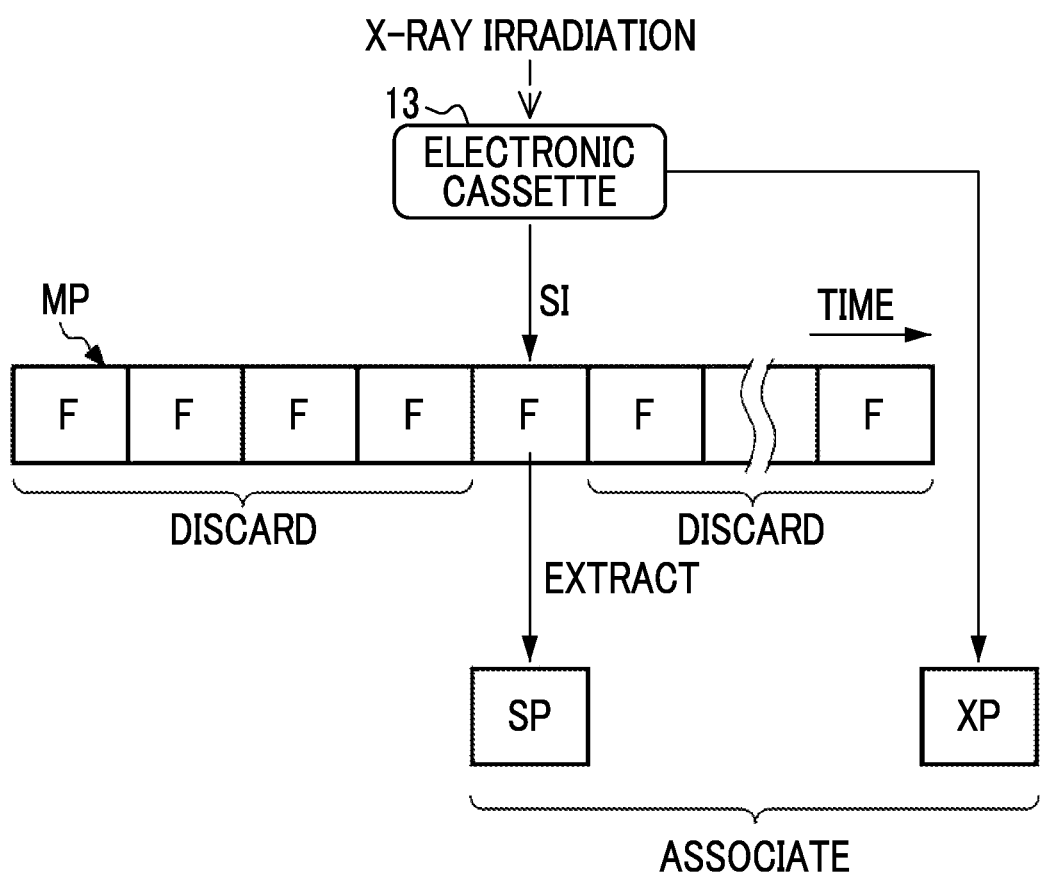
FIG. 16 is a diagram illustrating a still image acquisition process according to a modification example of a first embodiment.

Specifically, as shown in FIG. 16, the still image acquisition unit 62 extracts a frame F corresponding to a time point at which the irradiation start detection signal SI is received from the electronic cassette 13 from among a plurality of the frames F forming the motion picture MP acquired by the motion picture acquisition unit 65. The still image acquisition unit 62 uses the extracted frame F as the still image SP, and discards the remaining frames F other than the extracted frame F.

The still image acquisition unit 62 may store a time point at which the irradiation start detection signal SI is received from the electronic cassette 13, and may extract the frame F from the motion picture MP after the X-ray imaging is finished. In this case, the motion picture MP acquired by the motion picture acquisition unit 65 is stored in the storage device 54 or the like, the frame F corresponding to a time point at which the irradiation start detection signal SI is received is extracted as the still image SP, and then the motion picture MP is erased from the storage device 54 or the like.

The still image SP acquired by the still image acquisition unit 62 is associated with the X-ray image XP by the association unit 63 and stored in the storage device 54 similarly to the first embodiment.

Other configurations of the X-ray imaging system according to the present exemplary embodiment are the same as the configurations of the X-ray imaging system 10 according to the first embodiment.

Second Embodiment

Next, a second embodiment of the present disclosure will be described. In the first embodiment, the asynchronous electronic cassette 13 is used as a radiation image detector, but in the second embodiment, a synchronous electronic cassette 13B is used as a radiation image detector. In the present embodiment, the electronic cassette 13B starts an operation in response to receiving a control signal from the console 14. Thus, the irradiation start detection unit 33 is not provided in the electronic cassette 13B.

In the second embodiment, the console 14 transmits a preparation request signal REQ for requesting preparation for X-ray detection to the electronic cassette 13B before starting irradiation with X-rays from the X-ray source 11. Upon receiving the preparation request signal REQ, the electronic cassette 13B performs the above reset operation and the like, and then transmits a ready signal RDY indicating that preparation for X-ray detection has been completed to the console 14. The console 14 causes the optical camera 15 to capture a still image in conjunction with the ready signal RDY transmitted from the electronic cassette 13. The ready signal RDY is an example of a timing signal according to the technique of the present disclosure.

Figure 17:
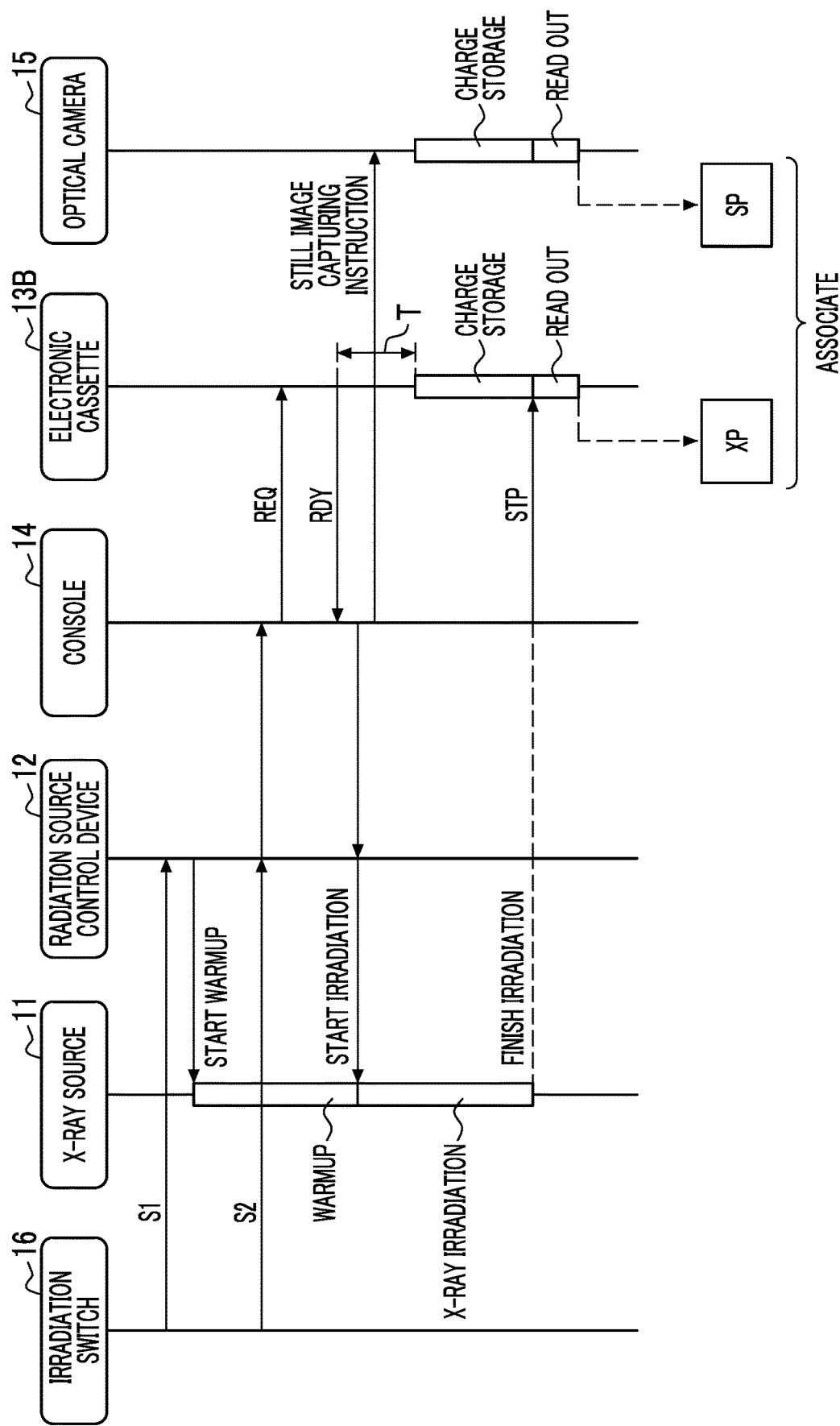
FIG. 17 is a sequence diagram showing an operation timing of each unit of an X-ray imaging system according to a second embodiment.

Next, an operation timing of each unit of the X-ray imaging system according to the second embodiment will be described more specifically. FIG. 17 is a sequence diagram showing the operation timing of each part of the X-ray imaging system according to the second embodiment. In the present embodiment, the irradiation switch 16 is the above two-step switch.

As shown in FIG. 17, in a case where the irradiation switch 16 is half-pressed, the irradiation switch 16 transmits a first operation signal S1 to the radiation source control device 12. Upon receiving the first operation signal S1, the radiation source control device 12 causes the X-ray source 11 to start warming up the X-ray tube 11A.

Next, in a case where the irradiation switch 16 is full-pressed, a second operation signal S2 is transmitted from the irradiation switch 16 to the radiation source control device 12. In a case where the radiation source control device 12 receives the second operation signal S2, the console 14 transmits the preparation request signal REQ to the electronic cassette 13B. The electronic cassette 13B transmits the ready signal RDY to the console 14 after performing a reset operation or the like. Upon receiving the ready signal RDY, the console 14 causes the X-ray source 11 to start applying X-rays. Upon receiving the ready signal RDY, the console 14 causes the still image capturing instruction unit 61 to instruct the optical camera 15 to execute still image capturing.

The electronic cassette 13B starts charge storage for X-ray imaging after a predetermined time T elapses from transmission of the preparation request signal REQ to the console 14. The predetermined time T is a value of 0 or more. After receiving the instruction for executing still image capturing, the optical camera 15 starts charge storage for still image capturing.

The console 14 transmits an irradiation end signal STP to the electronic cassette 13B after the predetermined X-ray irradiation time elapses. Upon receiving the irradiation end signal STP, the electronic cassette 13B performs a readout operation to generate the X-ray image XP. The optical camera 15 generates the still image SP by performing a readout operation after a predetermined exposure time elapses from starting of the charge storage.

Other configurations of the X-ray imaging system according to the second embodiment are the same as the configurations of the X-ray imaging system 10 according to the first embodiment.

Third Embodiment

Next, a third embodiment of the present disclosure will be described. In the first embodiment, the console 14 causes the optical camera 15 to execute still image capturing on the basis of the irradiation start detection signal SI transmitted from the electronic cassette 13. Alternatively, in the third embodiment, the console 14 causes the optical camera 15 to execute still image capturing on the basis of a signal transmitted from an automatic exposure controller provided separately from the electronic cassette 13.

Figure 18:
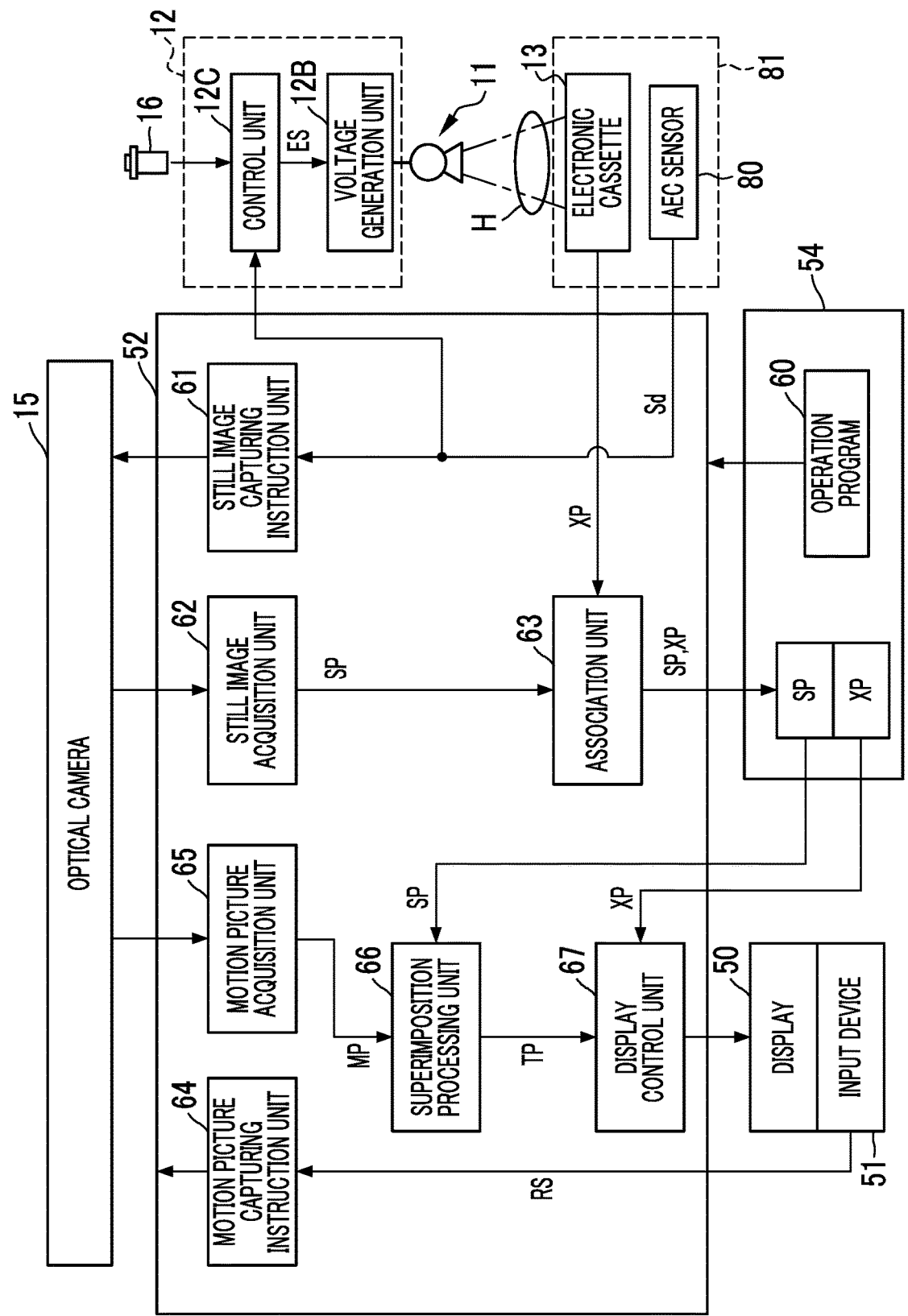
FIG. 18 is a diagram showing a configuration of an X-ray imaging system according to a third embodiment.

FIG. 18 is a diagram showing a configuration of an X-ray imaging system according to the third embodiment. As shown in FIG. 18, in the present embodiment, an automatic exposure control (AEC) sensor 80 as an automatic exposure controller is provided in the vicinity of the electronic cassette 13. In the present embodiment, the electronic cassette 13 is held on an imaging table 81. The imaging table 81 is an imaging table such as a standing position imaging table or a lying position imaging table. The AEC sensor 80 is held on the imaging table 81 and is disposed in front of or behind the electronic cassette 13.

The AEC sensor 80 is a sensor that measures a dose of X-rays transmitted through the subject H, and transmits a dose detection signal Sd to the console 14. The console 14 supplies the detection signal Sd to the control unit 12C of the radiation source control device 12. After irradiation with X-rays from the X-ray source 11 is started, the control unit 12C stops the irradiation with the X-rays from the X-ray source 11 in a case where a cumulative dose reaches a target dose on the basis of the dose detection signal Sd. This stoppage of the X-ray irradiation is performed even before the irradiation time included in the preset X-ray irradiation conditions is reached.

The dose detection signal Sd transmitted from the AEC sensor 80 to the console 14 is also supplied to the still image capturing instruction unit 61. In the present embodiment, the still image capturing instruction unit 61 instructs the optical camera 15 to execute still image capturing in response to receiving the detection signal Sd. The detection signal Sd is an example of a radiation detection signal output from the automatic exposure controller.

Other configurations of the X-ray imaging system according to the third embodiment are the same as the configurations of the X-ray imaging system 10 according to the first embodiment. Also in the present exemplary embodiment, similarly to the first embodiment, it is possible to reduce a difference between acquisition times of the X-ray image XP and the still image SP.

Each of the X-ray imaging systems according to the above embodiments is characterized in that an optical image acquired by an optical camera is associated with a radiation image on the basis of a timing signal transmitted from the radiation image detector side. By acquiring the optical image on the basis of the timing signal transmitted from the radiation image detector side, it is possible to reduce a difference between acquisition times of the radiation image and the optical image.

The modification example of the first embodiment shown in FIG. 16 can be applied to both the second embodiment and the third embodiment.

Each of the above embodiments has been described by exemplifying the X-ray imaging system provided in the imaging room, but the X-ray imaging system may be one using a so-called mobile visiting car.

The technique of the present disclosure can be applied not only to X-rays but also to a system for imaging a subject by using other radiation such as γ-rays.

In each of the above embodiments, hardware structures of processing units executing various processes, such as the still image capturing instruction unit 61, the still image acquisition unit 62, the association unit 63, the motion picture capturing instruction unit 64, the motion picture acquisition unit 65, the superimposition processing unit 66, and the display control unit 67 are various processors as described below.

The various processors include a CPU, a programmable logic device (PLD), a dedicated electric circuit, and the like. As is well known, the CPU is a general-purpose processor that executes software (program) and functions as various processing units. The PLD is a processor such as a field programmable gate array (FPGA) of which a circuit configuration can be changed after manufacturing. The dedicated electric circuit is a processor having a circuit configuration specially designed for executing a specific process, such as an application specific integrated circuit (ASIC).

One processing unit may be configured with one of these various processors, or may be configured with a combination of two or more processors of the same type or different types (for example, a plurality of FPGAs or a combination of a CPU and an FPGA). A plurality of processing units may be configured by one processor. As an example of configuring a plurality of processing units with one processor, first, there is a form in which one processor is configured by a combination of one or more CPUs and software, as typified by a computer used for a client or a server, and this processor functions as a plurality of processing units. Second, as typified by system on chip (SoC), there is a form in which a processor that realizes functions of the entire system including a plurality of processing units with one integrated circuit (IC) chip is used. As described above, the various processing units are configured by using one or more of the above various processors as a hardware structure.

The hardware structure of these various processors is, more specifically, an electric circuit (circuitry) in which circuit elements such as semiconductor elements are combined.

It goes without saying that the present invention is not limited to each of the above embodiments, and various configurations can be employed without departing from the concept of the present invention. The present invention is applied not only to a program but also to a storage medium storing the program in a non-transitory manner.

What is claimed is:

1. An imaging support device used in a radiography apparatus including a radiation source and a radiation image detector that detects a radiation image of a subject on the basis of radiation emitted from the radiation source and transmitted through the subject, the imaging support device comprising:
   an optical camera that acquires an optical image for each frame by optically imaging a region including an irradiation field of the radiation applied to the subject from the radiation source and outputs a motion picture formed of the acquired plurality of frames; and
   at least one processor,
   wherein the processor associates the optical image for one frame acquired by the optical camera with the radiation image as a still image on the basis of a timing signal transmitted from a radiation image detector side, superimposes the still image on each frame of the motion picture, and displays each superimposition image on a display, and
   wherein the radiation image associated with the still image is the radiation image in which a technician has determined that there is an imaging failure.

2. The imaging support device according to claim 1, wherein the timing signal is an irradiation start detection signal output from the radiation image detector having a radiation irradiation start detection function.

3. The imaging support device according to claim 1, wherein the timing signal is a radiation detection signal output from an automatic exposure controller provided separately from the radiation image detector.

4. The imaging support device according to claim 1, wherein the timing signal is a ready signal output in a case where the radiation image detector is ready to detect radiation.

5. The imaging support device according to claim 1, wherein the processor associates patient information with the associated still image and radiation image and outputs the associated still image and the radiation image with patient information.

6. An operation method for an imaging support device used in a radiography apparatus including a radiation source and a radiation image detector that detects a radiation image of a subject on the basis of radiation emitted from the radiation source and transmitted through the subject, the imaging support device including an optical camera that acquires an optical image for each frame by optically imaging a region including an irradiation field of the radiation applied to the subject from the radiation source and outputs a motion picture formed of the acquired plurality of frames, the operation method comprising:

associating the optical image for one frame acquired by the optical camera with the radiation image as a still image on the basis of a timing signal transmitted from a radiation image detector side, superimposes the still image on each frame of the motion picture, and displays each superimposition image on a display, wherein the radiation image associated with the still image is the radiation image in which a technician has determined that there is an imaging failure.

7. A non-transitory computer-readable storage medium storing an operation program for operating an imaging support device used in a radiography apparatus including a radiation source and a radiation image detector that detects a radiation image of a subject on the basis of radiation emitted from the radiation source and transmitted through the subject, the imaging support device including an optical camera that acquires an optical image for each frame by optically imaging a region including an irradiation field of the radiation applied to the subject from the radiation source and outputs a motion picture formed of the acquired plurality of frames, and at least one processor, the operation program causing the processor to execute:

associating the optical image for one frame acquired by the optical camera with the radiation image as a still image on the basis of a timing signal transmitted from a radiation image detector side, superimposes the still image on each frame of the motion picture, and displays each superimposition image on a display, wherein the radiation image associated with the still image is the radiation image in which a technician has determined that there is an imaging failure.

* * * * *